(12) United States Patent
Troiano

(10) Patent No.: US 9,920,253 B2
(45) Date of Patent: Mar. 20, 2018

(54) MICROORGANISM MEDIATED LIQUID FUELS

(71) Applicant: Somerset Coal International, Warrendale, PA (US)

(72) Inventor: Richard Troiano, Vandergrift, PA (US)

(73) Assignee: Somerset Coal International, Vandergrift, PA (US)

(*) Notice: Subject to any disclaimer, the term of this patent is extended or adjusted under 35 U.S.C. 154(b) by 65 days.

(21) Appl. No.: 14/133,449

(22) Filed: Dec. 18, 2013

(65) Prior Publication Data
US 2014/0162336 A1 Jun. 12, 2014

Related U.S. Application Data

(63) Continuation-in-part of application No. 12/620,245, filed on Nov. 17, 2009, now abandoned.
(Continued)

(51) Int. Cl.
*C10G 1/00* (2006.01)
*C10G 1/02* (2006.01)
(Continued)

(52) U.S. Cl.
CPC ............... *C10G 1/00* (2013.01); *C10G 1/002* (2013.01); *C10G 1/02* (2013.01); *C10G 32/00* (2013.01);
(Continued)

(58) Field of Classification Search
CPC . C10G 1/00; C10G 1/002; C10G 1/02; C10G 32/00; C12P 5/00
See application file for complete search history.

(56) References Cited

U.S. PATENT DOCUMENTS

| 4,511,460 A | 4/1985 | Baumert et al. |
| 4,624,417 A | 11/1986 | Gangi |

(Continued)

FOREIGN PATENT DOCUMENTS

WO 2013/177471 A2 11/2013

OTHER PUBLICATIONS

Hofrichter M, et al. Depolymerization of low-rank coal of extracellular fungal enzyme systems. II. The ligninolytic enzymes of the coal-humic-acid-depolymerizining fungus Nematoloma frowardii b19, 1997, Appl. Miicrobiol. Biotechnol. vol. 47, pp. 419-424.*

(Continued)

*Primary Examiner* — Renee Robinson
*Assistant Examiner* — Derek N Mueller
(74) *Attorney, Agent, or Firm* — Eversheds Sutherland (US) LLP

(57) ABSTRACT

Herein disclosed is a method for producing liquid hydrocarbon product, the method comprising disintegrating a hydrocarbon source; pretreating the disintegrated hydrocarbon source; solubilizing the disintegrated hydrocarbon source to form a slurry comprising a reactant molecule of the hydrocarbon source; admixing a biochemical liquor into the slurry, wherein the biochemical liquor comprises at least one conversion enzyme configured to facilitate bond selective photo-fragmentation of said reactant molecule of the hydrocarbon source, to form liquid hydrocarbons via enzyme assisted bond selective photo-fragmentation, wherein said conversion enzyme comprises reactive sites configured to restrict said reactant molecule such that photo-fragmentation favorably targets a preselected internal bond of said reactant molecule; separating the liquid hydrocarbons from the slurry, wherein contaminants remain in the slurry; and enriching the liquid hydrocarbons to form a liquid hydro-
(Continued)

carbon product. Various aspects of such method/process are also discussed.

18 Claims, 26 Drawing Sheets

Related U.S. Application Data

(60) Provisional application No. 61/141,552, filed on Dec. 30, 2008, provisional application No. 61/146,816, filed on Jan. 23, 2009.

(51) Int. Cl.
    *E21B 43/29*     (2006.01)
    *C10G 32/00*     (2006.01)
    *C12P 5/00*     (2006.01)

(52) U.S. Cl.
    CPC ............... *E21B 43/29* (2013.01); *C12P 5/00* (2013.01); *Y02P 20/582* (2015.11)

(56) References Cited

U.S. PATENT DOCUMENTS

| | | | |
|---|---|---|---|
| 4,793,656 | A | 12/1988 | Siddoway et al. |
| 4,882,274 | A | 11/1989 | Pyne et al. |
| 4,914,024 | A | 4/1990 | Strandberg et al. |
| 5,036,013 | A | 7/1991 | Wood et al. |
| 5,232,854 | A | 8/1993 | Monticello |
| 5,358,870 | A | 10/1994 | Monticello et al. |
| 2008/0190013 | A1 | 8/2008 | Argyropoulos |
| 2008/0305531 | A1 | 12/2008 | Lam et al. |
| 2010/0163460 | A1 | 7/2010 | Szuhay et al. |
| 2012/0144887 | A1 | 6/2012 | Fiato et al. |
| 2012/0259146 | A1 | 10/2012 | Gruber et al. |
| 2013/0131196 | A1 | 5/2013 | Michael et al. |

OTHER PUBLICATIONS

Perry's Chemical Engineers' Handbook, 7th Edition, 1997, pp. 13-4-13-5.*
Borole et al., "Improving Enzyme Activity and Broadening Selectivity for Desulfurization and Upgrading of Petroleum Feedstocks", Department of Energy, DE-FC07-00ID14000, dated 2003, pp. 1-9 (9 pgs.).
Goswami et al., "Hot Chemistry with Cold Molecules, Laser Pulse Phenomena and Applications", F.J. Duarte (ed.), dated 2010, pp. 371-389 (19 pgs.).
Gruebele et al., "Vibrational Energy Flow and Chemical Reactions", Acc. Chem. Res., vol. 37, dated 2005, pp. 261-267, (7 pgs.).
Toscano et al., "Minimalist Active-Site Redesign: Teaching Old Enzymes New Tricks", Angewandte Chem. Int., vol. 46, pp. 3212-3236, dated 2007 (25 pgs.).
Corkum et al., "Subfemtosecond Processes in Strong Laser Fields", Annual Reviews Phys. Chem., vol. 48, pp. 387-406, dated 1997 (20 pgs.).
Steinkruger, Jay, "Minimalist Enzymatic Active Site Redesign", The University of Wisconsin Madison, Department of Chemistry Gellman Group, dated Mar. 13, 2008, pp. 1-37 (37 pgs.).
Jiang et al., "Submolecular Control, Spectroscopy and Imaging of Bond-Selective Chemistry in Single Functionalized Molecules", Nature Chemistry, DOI 10.1038/NCHEM.1488, dated Nov. 11, 2012, pp. 1-6 (6 pgs.).
Scherer et al., "Realtime Picosecond Clocking of the Collision Complex in a Bimolecular Reaction: The Birth of OH from H+CO2", The Journal of Chemical Physics, vol. 87, No. 2, dated Jul. 15, 1987, pp. 1451-1453 (4 pgs.).
Diau et al., "Femtosecond Activation of Reactions and the Concept of Nonergodic Molecules", Science, vol. 279, dated Feb. 6, 1998, pp. 847-851 (5 pgs.).

Rothlisberger et al., "Kemp Elimination Catalysts by Computational Enzyme Design", Nature Publishing Group, vol. 453, dated May 8, 2008, pp. 190-197, (8 pgs.).
Frohnmeyer et al., "Mapping Molecular Dynamics (Na2) in Intense Laser Fields: Another Dimension to Femtochemistry", Elsevier, Chemical Physics Letters, vol. 312, dated Oct. 29, 1999, pp. 447-454 (8 pgs.).
Chemical and Engineering News, "Process Yields Diesel-Like Fuel From Coal, Peat, Biomass", dated Jul. 1, 1985, pp. 23-24 (2 pgs.).
Green, Don W. editor, "Gravity Sedimentation Operations", Perry's Chemical Engineers Handbook, 7th Ed., dated 1997, pp. 18-59-18-60 (4 pgs.).
Zewail, Ahmed H., "Femtochemistry: Atomic-Scale Dynamics of the Chemical Bond Using Ultrafast Lasers (Nobel Lecture)", Wiley-VCH Verlag GmbH, ISBN: 3-527-60018-3, dated 2001, pp. 58-62 (85 pgs.).
Search Report and Written Opinion dated Jul. 5, 2013 for International Application No. PCT/US2009/064801 (9 pgs.).
Office Action dated Jun. 19, 2013 for U.S. Appl. No. 12/620,245 (12 pgs.).
Office Action dated Jan. 31, 2013 for U.S. Appl. No. 12/620,245 (13 pgs.).
Office Action dated Jun. 7, 2012 for U.S. Appl. No. 12/620,245 (13 pgs.).
Troiano, Richard, "Enzymatic Conversion of Coal to Liquid Fuels", Final Report for the U.S. Dept. of Energy, Coal Fuel Systems, Vandergrift, PA, dated 2011 (48 pgs.).
Search Report and Written Opinion dated Mar. 23, 2015 for corresponding International Application No. PCT/US2014/069879 (14 pgs.).
Wise, D. L. "Bioprocessing and Biotreatment of Coal," Marcel Dekker, New York, dated 1990, p. 34 (2 pgs.).
Fleming, I., "Molecular Orbitals and Organic Chemical Reactions," Department of Chemistry, University of Cambridge, (UK), Wiley & Sons Ltd., dated 2006, pp. 32-35 (4 pgs.).
Kirk, et al., "Enzymatic "Combustion": The Microbial Degradation of Lignan," Annual Review of Microbiology, dated 1987, vol. 41, pp. 465-505 (41 pgs.).
Deacon, J. W., "Fungal Ecology: Saprotrophs," Fungal Biology 4th Ed., Malden, MA, Blackwell Publishing, dated 2006, pp. 229-235 (8 pgs.).
Neujahr, H. Y., "Yeast in Biodegradation and Biodeterioration Processes," Biotechnology and Biocatalysis, New York, dated 1978, pp. 321-329, 332-348 (15 pgs.).
Ralph, J. P., "Biodeterioration by White-Rot Fungi," The Mycotta X—Industrial Applications, Osiewacz, Springer-Verlag, Berlin Heidelberg, dated 2002, pp. 303-326 (19 pgs.).
Gold et al., "Metal Ions in Biological Systems," Manganese and Its Role in Biological Processes, Marcel Dekker, New York, vol. 37, dated 2000, pp. 573-577 (6 pgs.).
Bryant, J. R., "Mechanistic Studies of the Oxidation of Hydrocarbons by Manganese and Ruthenium Transition Metal Complexes," Doctoral Dissertation, University of Washington, Seattle, WA, dated 2002 (142 pgs.).
Atkins et al., "Inorganic Chemistry," Oxford University Press, Oxford, UK, dated 2006, p. 467 (2 pgs.).
Crabtree, R. H., "Types of Ligand," The Organometallic Chemistry of the Transition Metals, Wiley & Sons, Hoboken, NJ, dated 2009, pp. 26-29 (2 pgs.).
Larsen, et al., "Introduction to Manganese Enzymes in Manganese Redox Enzymes," VCH Publishers, New York, dated 1992, p. 3 (2 pgs.).
Stultz, et al., "Distortions of the Coordination Polyhedron in High-Spin Manganese (III) Complexes. 3. Crystal and Molecular Structure of y-Tris(acetylacetonato)manganese (III): A Tetragonally Elongated Octahedral Form," Inorg. Chem. vol. 18, No. 7, dated 1979, pp. 1853-1858 (6 pgs.).
Avdeef et al., "Crystal and Molecular Structure of Tris(tropolonato)manganese (III), Mn(O2C7H5)3, a High-Spin Complex Having Structural Features Consistent with Jahn-Teller Behavior for two Distinct MnO6 Centers," Inorg. Chem. vol. 13, No. 8, dated 1974, pp. 1854-1863 (10 pgs.).

(56) References Cited

OTHER PUBLICATIONS

Fackler et al., "Crystal and Molecular Structure of Tris(2,4-pentanedionato)manganese (III), Mn(O2C5H7)3 a Distorted Complex as Predicted by Jahn-Teller Arguments," Inorg. Chem. vol. 13, No. 8, dated 1974, 1864-1875 (12 pgs.).
Levine et al., "Molecular Reaction Dynamics and Chemical Reactivity," Oxford University Press, New York, dated 1987, p. 373 (2 pgs.).
Assion et al., "Control of Chemical Reactions by Feedback-Optimized Phase-Shaped Femtosecond Laser Pulses," Science, vol. 282, dated Oct. 30, 1998, pp. 919-922 (5 pgs.).
Bigwood et al., "Freezing molecular vibrational energy flow with coherent control," Journal of Molecular Structure (Theochem), 2002, 589-590, pp. 447-457.
Cui et al., "The role of manganese in model systems related to lignin biodegradation," Holzforschung, 1990, 44, 4, pp. 279-283.
Forrester et al., "Manganese, Mn-dependent peroxidases, and the biodegradation of lignin," Biochemical and Biophys Res Comm, 1988 157, 3, pp. 992-999.
Glenn et al., "Mn(II) oxidation is the principal function of the extracellular Mn-peroxidase from Phanerochaete chrysosporium," Archives of Biochemistry and Biophys, 1986, 251, 2, pp. 688-696.
Glenn et al., "Purification and characterization of an extracellular Mn(II)-dependent peroxidase from the lignin-degrading basidiomycete, Phanerochaete chrysosporium," Archives of Biochemistry and Biophys, 1985, 242, 2, pp. 329-341.
Gonzalez Gemma M.E., "Enzymatic degradation of polycyclic aromatic hydrocarbons (PAHs) by manganese peroxidase in reactors containing organic solvents," PhD Dissertation, University of Santiago de Compostela Department of Chemical Engineering, 2007 (209 pages).

Hofrichter et al., "Degradation of lignite (low-rank coal) by ligninolytic basidiomycetes and their manganese peroxidase system," Appl Microbial Biotechnol, 1999, 52, pp. 78-84.
Leatham et al., "Degradation of Phenolic Compounds and Ring Cleavage of Catechol by Phanerochaete chrysosporium," Appl and Environmental Microbial, 1983, 46, 1, pp. 191-197.
Manikandan et al., "Dynamical traps lead to the slowing down of intramolecular vibrational energy flow," PNAS, 2014, 111, 40, pp. 14354-14359.
Paszcynski et al., "Comparison of ligninase-I and peroxidase-M2 from the white-rot fungus Phanerochaete chrysosporium," Archives of Biochemistry and Biophys, 1986, 244, 2, pp. 750-765.
Wariishi et al., "In Vitro Depolymerization of Lignin by Manganese Peroxidase of Phanerochaete chrysosporium," Biochemical and Biophys Res Comm, 1991, 176, 1, pp. 269-275.
Wariishi et al., Manganese (II) Oxidation by Manganese Peroxidase from the Basidiomycete Phanerochaete chrysosporium: Kinetic Mechanism and Role of Chelators, 1992, 267, 33, pp. 23688-23695.
Wariishi et al., "Manganese Peroxidase from the Basidiomycete Phanerochaete chrysosporium: Spectral Characterization of the Oxidized States and the Catalytic Cycle," Biochemistry, 1988, 27, pp. 5365-5370.
Wariishi et al., "Manganese Peroxidase from the Lignin-degrading Basidiomycete Phanerochaete chrysosporium," The Journal of Biological Chemistry, 1989, 264, 6, pp. 3335-3340.
Wariishi et al., "Oxidative Cleavage of a Phenolic Diarylpropane Lignin Model Dimer by Manganese Peroxidase from Phanerochaete chrysosporium," Biochemistry, 1989, 28, pp. 6017-6023.
Wilkie et al., "Time-Dependent Manifestations of Quantum Chaos," Physical Review Letters, 1991, 67, 10, pp. 1185-1188.
European Search Report for EP Application No. 14872224.2 dated Jul. 28, 2017 (9 pages).

* cited by examiner

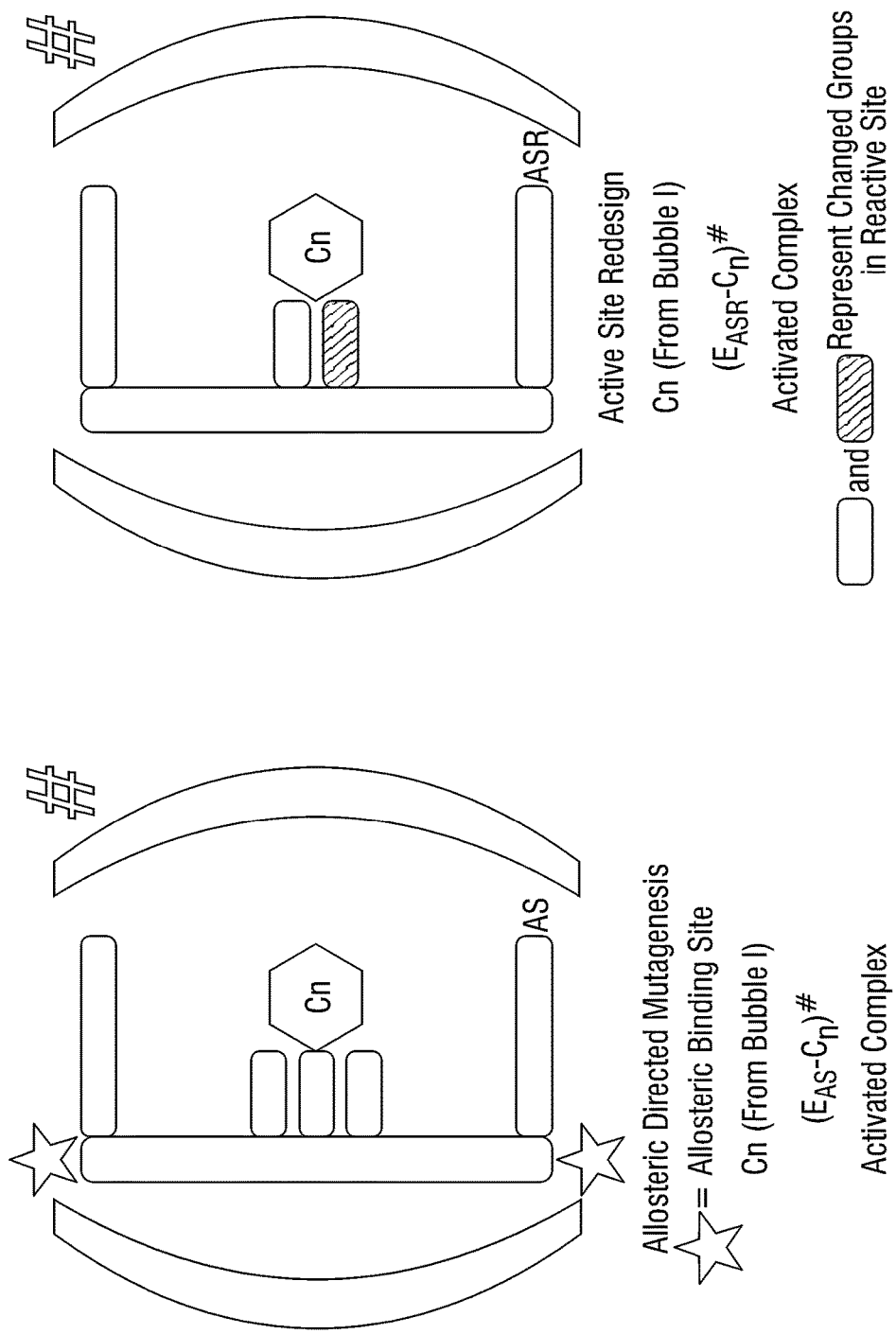

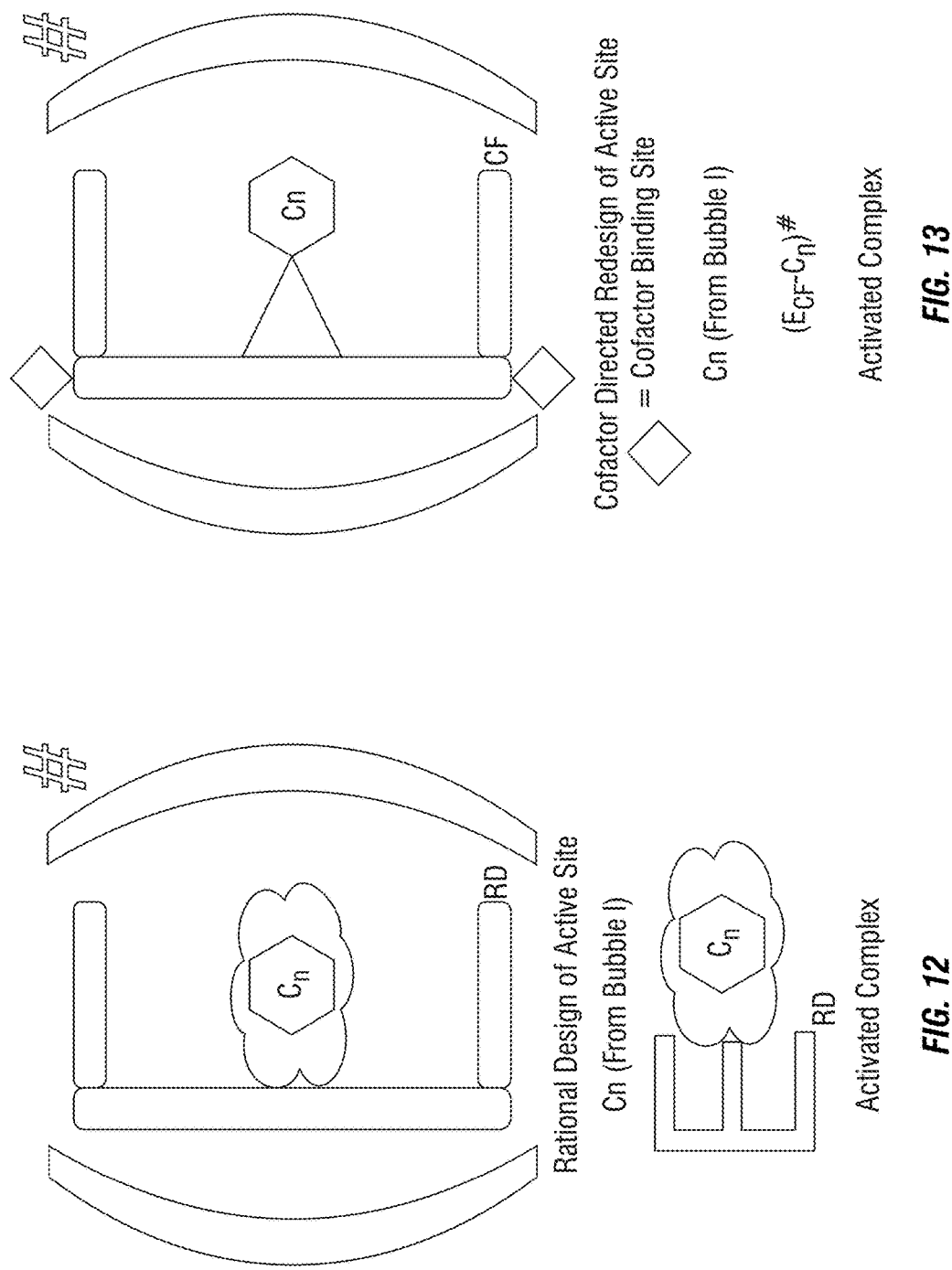

Shaped IR Femtosecond Laser Pulses for Directed Fragmentation at Enzymatically Strained, Selective Bonds Within $C_n$ Reactants from Bubble I ⟵⟶ Represent Non Covalent Bonds Between Enzymes/ Enzyme-Like Structures and $C_n$ Reactants from Bubble I. $C_n$ Reactants Depicted as Ring Structures for Illustration Purposes Only

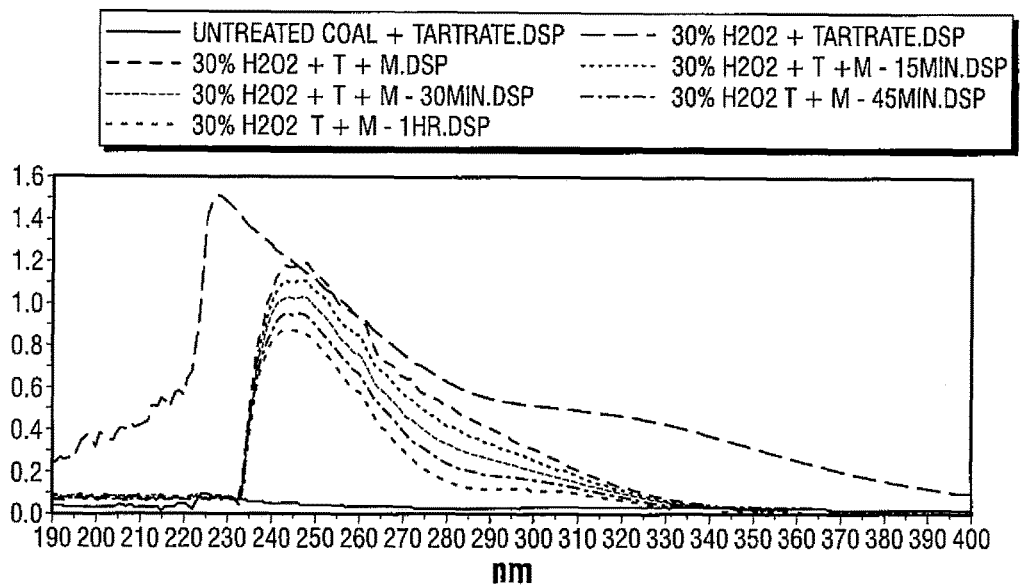
FIG. 19J
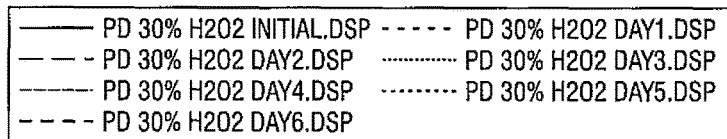
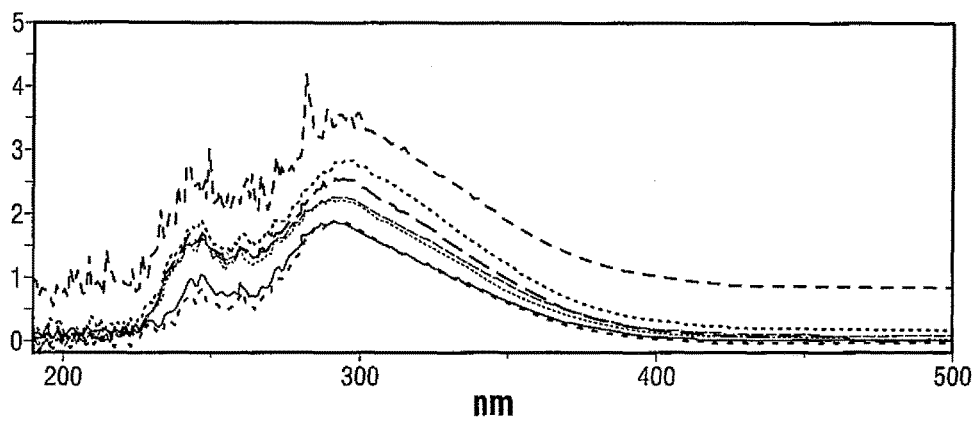
FIG. 19K

MICROORGANISM MEDIATED LIQUID FUELS

CROSS-REFERENCE TO RELATED APPLICATIONS

This application is a continuation-in-part application of U.S. patent applicant Ser. No. 12/620,245 filed Nov. 17, 2009, which claims benefit under 35 U.S.C. § 119(e) of U.S. Provisional Patent Application No. 61/141,552 filed Dec. 30, 2008 and U.S. Provisional Patent Application No. 61/146,816 filed Jan. 23, 2009. The disclosures of these three applications are hereby incorporated herein by reference.

STATEMENT REGARDING FEDERALLY SPONSORED RESEARCH OR DEVELOPMENT

A portion of this work was supported by federal funding under contract number DOE/NETL award: DE-FE0001259.

BACKGROUND

Field of the Invention

This invention relates to producing liquid fuels, specifically to in-situ or ex-situ coal to liquid conversion.

Background of the Invention

Coals can also be converted into liquid fuels like gasoline or diesel by several different processes. In a developing commercial process, the coal converted into a gas first, and then into a liquid, by using the Fischer-Tropsch (FT) process. In the FT process, an indirect route, coal is first gasified to make syngas, a purified mixture of CO and $H_2$ gas. Next, FT catalysts are used to convert the syngas into light hydrocarbons, like ethane, which are further processed into refinable liquid fuels. In addition to creating the fuels, syngas can also be converted into methanol, which can be used as a fuel, or a fuel additive.

Alternatively, the coal may be converted directly to liquid fuels via hydrogenation processes. For example, the Bergius process, in which coal is liquefied by mixing it with hydrogen gas and heating the system. Several other direct liquefaction processes have been developed, such as the Solvent Refined Coal (SRC) processes, which has spawned several pilot plant facilities. Additionally, dried, pulverized coal mixed with roughly 1 wt % molybdenum catalysts may be hydrogenated by use of high temperature and pressure synthesis gas produced. However, the syngas must be produces in a separate gasifier.

However, these coal to liquid fuel processes involve the mining of the coal from the ground. As is well documented, coal mining is a hazardous process, and many mines are forced into closure prior to the removal of all useable products. Further, those mines that are operated safely leave behind large columns of coal to support the ceiling and coal residues in the mine walls. These sources of coal represent a significant amount of energy that is left abandoned by mining operations. Further, these untouched resources may be converted to liquid fuels for transportation purposes. As such, there is a need in the industry for the removal of abandoned, low quality, or residual coal from mining operations, for use in the coal to liquid production.

SUMMARY

Herein disclosed is a method for producing liquid hydrocarbon product, the method comprising disintegrating a hydrocarbon source; pretreating the disintegrated hydrocarbon source; solubilizing the disintegrated hydrocarbon source to form a slurry comprising a reactant molecule of the hydrocarbon source; admixing a biochemical liquor into the slurry, wherein the biochemical liquor comprises at least one conversion enzyme configured to facilitate bond selective photo-fragmentation of said reactant molecule of the hydrocarbon source, to form liquid hydrocarbons via enzyme assisted bond selective photo-fragmentation, wherein said conversion enzyme comprises reactive sites configured to restrict said reactant molecule such that photo-fragmentation favorably targets a preselected internal bond of said reactant molecule; separating the liquid hydrocarbons from the slurry, wherein contaminants remain in the slurry; and enriching the liquid hydrocarbons to form a liquid hydrocarbon product.

In an embodiment, disintegrating the hydrocarbon source comprises comminution of the hydrocarbon source. In an embodiment, comminution comprises grinding. In an embodiment, comminution comprises high-pressure steam treatment. In an embodiment, pretreating the disintegrated hydrocarbon source comprises chemical pretreatment, heat pretreatment, oxidation of the hydrocarbon source, or a combination thereof.

In an embodiment, solubilizing the disintegrated hydrocarbon source comprises treating the disintegrated hydrocarbon source with at least one enzyme. In an embodiment, admixing biochemical liquor comprises admixing at least one additional enzyme. In an embodiment, admixing at least one additional enzyme further comprises admixing an enzyme for converting a hydrocarbon source to lower molecular weight hydrocarbons.

In an embodiment, separating liquid hydrocarbons comprises a process of settling the slurry from the liquid hydrocarbon. In an embodiment, separating liquid hydrocarbons comprises settling contaminants from the liquid hydrocarbon. In an embodiment, enriching the liquid hydrocarbon comprises admixing the liquid hydrocarbon with at least one enzyme.

In an embodiment, the biochemical liquor comprises a modified enzyme. In an embodiment, the modified enzyme comprises an enzyme that is genetically modified. In an embodiment, the modified enzyme comprises an enzyme that is chemically modified.

In an embodiment, the method is conducted in-situ in a coal mine or ex-situ on mined coal. In an embodiment, enriching the liquid hydrocarbons comprises improving the liquid hydrocarbon product qualities prior to distillation. In an embodiment, the liquid hydrocarbon product comprises at least one selected from the group consisting of gasoline, diesel, kerosene, and distillates thereof. In an embodiment, the hydrocarbon source comprises at least one selected from the group consisting of coal, anthracite coal, bituminous coal, lignite, sub-bituminous coal, low-rank coals, coke, tar sand, and oil shale.

Herein also disclosed is a method for in-situ coal to liquid hydrocarbon conversion, comprising: locating an underground coal seam; drilling at least one well, the well in contact with the underground coal seam and having a means to cycle liquids therethrough; pressurizing the underground coal seam with steam; cycling reactants through the underground coal seam, wherein the reactants comprise at least one enzyme, to form a slurry; withdrawing a portion of the slurry; processing the slurry to produce the liquid hydrocarbon; separating the liquid hydrocarbon from the slurry; and returning the slurry to the coal seam for further processing.

In an embodiment, the at least one well is in fluid communication with a reactant stream. In an embodiment, the at least one well is in fluid communication with a slurry processing stream.

In an embodiment, cycling reactants to form a slurry further comprises solubilizing the coal to form a slurry; converting the coal to form liquid hydrocarbons; separating contaminant compounds from the liquid hydrocarbons, wherein the contaminant compounds comprise pollutants; settling the slurry from the liquid hydrocarbons, wherein the liquid hydrocarbons are suitable for liquid fuels; and processing the liquid hydrocarbons to liquid fuels.

In an embodiment, the step of solubilizing the coal comprises treating the coal with at least one enzyme. In an embodiment, the step of converting the coal comprises treating the coal with at least one enzyme. In an embodiment, the step of separating contaminant compounds comprises treating the liquid hydrocarbons with at least one enzyme.

Further disclosed is a method for using an enzyme to produce liquid fuels, comprising selecting a microorganism, the microorganism producing an enzyme; modifying a microorganism genetically, to increase the production of the enzyme; modifying the enzyme structurally, to alter the activity of the enzyme, to form a modified enzyme; collecting the modified enzyme, to form a biochemical liquor comprising at least one modified enzyme; and exposing a hydrocarbon source to the biochemical liquor to form a liquid fuel precursor.

In an embodiment, the step of selecting a microorganism comprises selecting at least one microorganism chosen from the group consisting of hypoliths, endoliths, cryptoliths, acidophiles, alkaliphiles, thermophiles, ithoautotrophs, halophiles, piezophiles, and combinations thereof. In an embodiment, modifying a microorganism comprises inserting a nucleic acid vector. In an embodiment, modifying a microorganism genetically comprises directed mutagenesis. In an embodiment, modifying an enzyme comprises structurally changing an enzyme. In an embodiment, exposing the biochemical liquor to the hydrocarbon source further comprises transmitted-radiation directed fragmentation.

In one embodiment, a method for producing liquid hydrocarbon products, comprising, disintegrating a hydrocarbon source, treating the disintegrated hydrocarbon source chemically, solubilizing the disintegrated hydrocarbon source, admixing a biochemical liquor, wherein the biochemical liquor comprises at least one enzyme to form liquid hydrocarbons, separating liquid hydrocarbons, and enriching the liquid hydrocarbons to form a liquid hydrocarbon product.

In another embodiment, a method for in-situ coal to liquid hydrocarbon conversion, comprising, locating an underground coal seam, drilling at least one well, the well in contact the underground coal seam; pressurizing the underground coal seam with steam; cycling reactants through the underground coal seam, wherein the reactants comprise at least one enzyme, to form a slurry; withdrawing a portion of the slurry; processing the slurry, wherein the liquid hydrocarbon is separated from the slurry; and returning the slurry to the coal seam for further processing.

In further embodiments, a method for using an enzyme to produce liquid fuels, comprising selecting a microorganism, the microorganism producing an enzyme; modifying a microorganism genetically, to increase the production of the enzyme; modifying the enzyme structurally, to alter the activity of the enzyme, to form a modified enzyme; collecting the modified enzyme to form a biochemical liquor comprising at least one modified enzyme; and exposing a hydrocarbon source to the biochemical liquor to form a liquid fuel precursor.

The foregoing has outlined rather broadly the features and technical advantages of the invention in order that the detailed description of the invention that follows may be better understood. The various characteristics described above, as well as other features, will be readily apparent to those skilled in the art upon reading the following detailed description of the preferred embodiments, and by referring to the accompanying drawings.

BRIEF DESCRIPTION OF THE DRAWINGS

For a detailed description of the preferred embodiments of the invention, reference will now be made to the accompanying drawings if various embodiments of the invention, in which:

FIG. 10 illustrates a representative diagram of allosteric directed mutagenesis of an activated enzyme complex.

FIG. 11 illustrates a representative diagram of an active site redesign of an activated enzyme complex.

FIG. 12 illustrates a representative diagram of an active site rational design of an activated enzyme complex.

FIG. 13 illustrates a representative diagram of a cofactor directed active site redesign of an activated enzyme complex.

FIG. 19J illustrates the results from the 30% H2O2 pretreated coal in chemical solubilization and conversion.

FIG. 19K illustrates the results from the 30% H2O2 pretreated coal in PD growth medium containing *P. chrysosporium*.

DETAILED DESCRIPTION OF THE PREFERRED EMBODIMENTS

Figure 1:
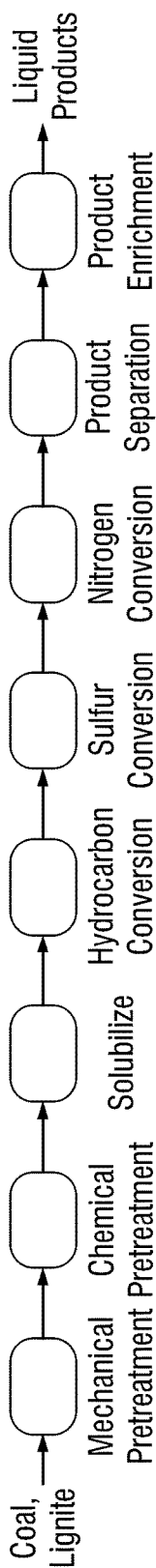
FIG. 1 illustrates a general flow process schematic for converting coal to liquid.

A process for converting coal to liquid fuels is disclosed. Coal comprises any coal found or removed from a coal mine, seam, or pit. The coal may further comprise anthracite coals, or the coke from bituminous coal. In certain instances, the coal comprises lignite, sub-bituminous coal, other low-rank coals, and/or other hydrocarbon source, such as tar sands, without limitation. Alternatively, the coal comprises weathered, aged, leached, or degraded coal without limitation.

In certain instances, the coal is converted to liquid fuels by a two-stage process. The process comprises ezymatically-catalyzed reactions. The first stage, Stage I, comprises the pretreatment and conversion of coal into liquid products by enzymes. In embodiments, Stage I converts coal feedstocks to liquid hydrocarbons. The feedstocks comprise coal remaining in coal mines, or in-situ feedstocks. Alternatively, the feedstocks comprise coal away from the coal mine, or ex-situ feedstocks. In certain instances, the source of hydrocarbons may comprise any source, such as tar sands, not preferred for other industries.

The second stage, Stage II, comprises the enrichment of the liquid hydrocarbon products. The enrichment, or improvement, of the liquid hydrocarbon product comprises further enzymatically-catalyzed reactions. Additionally, the reactions are enzyme-mediated processing steps. Stage II further comprises the improvement of the liquid product properties for use in fuels. The Stage II enzymatically-catalyzed processes change the fuel performance. In exemplary instances, Stage II processing may alter the cetane rating of diesel, or the octane rating of gasoline.

Compared to current processing techniques, the enzymatically-mediated two-stage process requires less energy for processing. Additionally, the reaction conditions are milder, as the enzymes perform optimally in homeostatic conditions of the microorganism producer. Further, additional enzymes or microorganisms may be implemented to sequester contaminants regulated in liquid fuels. For instance, sulfur and nitrogen may be reduced or removed from the liquid fuels prior to final product distillation. The early removal of polluting contaminants makes the process adjustable to meet current and future emissions regulations. Additionally, the enzyme-mediated two-stage process is adaptable to feedstocks previously inaccessible, for instance, coal columns in a mine too dangerous for removal by retreat mining.

Microorganisms.

In the disclosed process, microorganism-produced enzymes mediate the conversion. In embodiments, the microorganisms comprise bacteria, algae, or fungi. In certain instances, the microorganisms comprise heterotrophs that secrete enzymes for catalytic digestion of hydrocarbons. The microorganisms use hydrocarbons as a carbon source for life processes. The microorganisms are harvested from oil shales, oil sands, coal tar pits, or coal caves without limitation. For example, the microorganisms may be derived from those found in the La Brea Tar Pits. Further, the microorganisms may be collected from geothermal springs, mud volcanoes, sulfur cauldrons, fumaroles, geysers, mudpots, or the like, without limitation. The microorganisms may further comprise extremophiles, such as but not limited to hypoliths, endoliths, cryptoliths, acidophiles, alkaliphiles, thermophiles, ithoautotrophs, halophiles, or piezophiles. In exemplary embodiments, the microorganisms comprise archaebacteria. Alternatively, suitable microorganisms include those found in the geneses *Poria, Polyporus, Thiobacillus, Candida, Streptomyces, Psuedomonas, Penicillium,* or *Trichoderma*. As understood by one skilled in the art, alternative microorganisms may be identified that are suitable for application in the disclosed system, without being named specifically, that do not vary in structure and function significantly. Further, it can be envisioned that these microorganisms are envisioned as means to alter, improve, or modify the current disclosure.

In certain instances, the microorganisms are exposed to previously mined coal, coal residues, or coal residues less favorable for power production in order to harvest the enzymes. In instances, the microorganism produces the enzymes naturally. As understood by one skilled in the art, continued exposure to the substrate, such as coal, will lead to increased expression and production of the enzymes for the liquid hydrocarbon production.

Enzymes.

The enzymes used in the disclosed process are obtained from microorganisms that produce these enzymes in high yields. In further embodiments, the microorganisms are genetically altered to produce the enzymes in high yields. Preferably, the enzymes are secreted extracellularly and/or release the enzymes into their environment. Alternatively, the cells are lysed and the enzymes are captured for use in coal processing. In embodiments, the enzymes are separated from the microorganisms prior to use in the processing of coal. In order to reduce exposure, release, or environmental contamination, the microorganisms are separated from the processing. No microorganisms are directly involved in any embodiments of the liquid fuel production process. Furthermore, the facilities used to grow these organisms have sufficient provisions to isolate host organisms from the natural environment.

Alternatively, the microorganisms undergo site-directed mutagenesis to up-regulate, over-express, and/or increase, the production of enzymes. Site directed mutagenesis comprises the mutation of a DNA molecule at specific nucleic-acid base-pair sequence. Site directed mutagenesis may occur in the chromosomal DNA, or in extra-chromosomal DNA, from a vector. Additionally, the site-directed mutagenesis may comprise gene deletion/excision, primer mediated mutagenesis, cassette mutagenesis, add-on mutagenesis, mismatch mutagenesis, gene conversion, topological manipulation, specialized recombination, or PCR-mediated mutagenesis. Further, mutagenesis and over-expression of a gene may be induced by any mutagen. For instance, ionizing radiation, UV exposure, deamination, intercalation, alkylation, analog insertion, transposon multiplication, and other molecular biology techniques may be used, without limitation. In certain instances, mutagen exposure induces the microorganism to acquire a vector, such as a plasmid. Further, mutagenesis may induce the incorporation of vector DNA into the chromosomal DNA. For the purpose of this disclosure, directed, mutagenic technique may be implemented in order to induce additional production of an enzyme. Further, the mutagenesis may be used to increase the activity of the enzyme.

In certain instances, the enzymes are chemically modified after production. The enzymes may be modified prior to or after harvesting from the microorganisms. Any process known to one skilled in the art may be implemented, such as but not limited to addition of functional groups, addition of other peptides, altering the chemical nature, and/or structural changes. For example, processes like acylation, glycosylation, ubiquitination, deamidation, and/or cleavage, are envisioned to have applications within the present disclosure, without limitation.

The produces and modified enzymes are utilized in biochemical liquor. The biochemical liquor comprises a liquid mixture of proteins, enzymes, inorganic catalysts, and organic and inorganic compounds. The biochemical liquor further comprises salts, electrolytes, metals, and/or other molecules that aid, improve, or alter the operations of an enzyme broth, or biochemical liquor. The biochemical liquor is a mixture of at least one of each of the aforementioned groups without limitation. The biochemical broth may be suspended in any known solvent; preferably organic solvents. In exemplary embodiments, water is the solvent.

Process.

As illustrated in FIG. 1, the process comprises a flow of coal through a sequence of individual treatment steps. In STAGE I, the process comprises at least one pretreatment step. The coal then undergoes solubilization, which may be included in the pretreatment steps. The pretreated, solubilized coal material is converted to liquid hydrocarbons. Simultaneously, or sequentially, the material may undergo sulfur and nitrogen conversion. Removing sulfur and nitrogen from the product improves performance of the fuel after processing, such as separation. The different fuels are separated, such that aqueous phase reactants are recycled, and/or the wastewater is treated for return to the system. In STAGE II, the hydrocarbon phase products from the conversion step are further refined. The refining of the products comprises fuel refining, enrichment, and distillation to improve product qualities.

Pretreatment.

The pretreatment step comprises a physical and chemical degradation of the coal, to produce a degraded coal. In order to increase efficiency of the disclosed process it is advantageous to increase the surface area of the material. The surface area of the coal may be increased by reducing the particle volume, such as in the process of comminution. For instance, surface coal, mined coal, coal tailings, or remaindered coal is mechanically broken down or crushed into a fine particulate. Remaindered coal may comprise, without limitation, coal sourced from any industry from which it was rejected for use. The particulate may comprise pebbles, dusts, powders, or the like without limitation.

In certain instances, the coal is treated in-situ, for instance, in an underground coal seam, by high-pressure steam. Underground wells, conduits, and/or other lines deliver steam to a coal mine. The steam may be pressurized, superheated, or combinations thereof in order to increase penetration into the seam. The steam is used to fracture the coal bed underground prior to pretreatment. Further, the high-pressure steam mechanically separates the coal from surrounding rock formations.

Additionally, the coal is subjected to a chemical treatment. Chemical treatment of the coal increases the reactivity of the coal. Additionally, chemical treatment is designed to remove, digest, or eliminate non-coal materials from the coal products. Further, the chemical treatment may increase the surface area of the coal further by inducing the formation of pores, cavities, pits, and the like. The chemical treatment may compromise an oxidative agent. In certain embodiments, mild ionic, acid, base, or free radical solutions are applied to oxidize the coal. In an embodiment, the solution comprises a mild acid solution. In an exemplary embodiment, the chemical treatment comprises hydrogen peroxide. The hydrogen peroxide is in concentrations between about 10% and about 50%; alternatively between about 20% and about 40%, and in preferably about 30% hydrogen peroxide. As discussed above, the solutions are injected into coal mines with steam, or water, therefore it is preferable the solutions are aqueous. In certain instances, an inorganic chemical treatment may be implemented.

Solubilization.

Further, the pretreatment steps comprise solubilization of the degraded coal. Once mechanically disintegrated, and chemically oxidized, a first set of enzymes is introduced to break the cross-linking bonds in coal. In certain instances, the first enzymes may be derived from enzymes found, for example, in the genera *Peoria, Polypore's*, genuses *Poria, Polyporus*, without limitation. The first enzymes allow the coal particles to dissolve into the liquid medium. In embodiments, the liquid medium is the same as is used to deliver the enzymes. In certain instances, the medium is the biochemical liquor described above. Further, the liquid medium comprises an aqueous medium. The solubilized coal particles are suspended in the liquid medium forming a coal slurry; alternatively, a coal suspension, a coal mixture, a coal colloid, or a coal solution, without limitation. The coal slurry improves accessibility to the coal particles by the enzymes from the biochemical liquor. Suspending the particles in the medium may improve reaction kinetics during the subsequent enzymatically mediated steps. The coal slurry further improves transfer of the coal between processing steps.

Conversion.

After solubilization, the coal is processed by conversion steps. In certain instances, the solubilized coal in the coal slurry is converted to smaller or lower hydrocarbons. The lower hydrocarbons may comprise any hydrocarbon, for instance hydrocarbons comprising between about 24 carbons and about 2 carbons. The second enzyme, or second enzyme solution, is maintained in the biochemical broth. The second enzyme solution may be derived from enzymes produced by microorganisms for the genera, *Thiobacillus, Candida, Streptomyces, Psuedomonas, Penicillium, Trichoderma*, for example, without limitation. The second enzyme may be introduced to the coal slurry during the conversion process. In certain instances, the exposure of the coal slurry to a second enzyme comprises converting coal to lower molecular weight hydrocarbon fractions. Alternatively, the second enzyme is a converting enzyme. Converting enzymes are those selected, engineered, or modified to catalytically convert large hydrocarbon molecules found in coal to lower molecular weight hydrocarbons. During the conversion step, the hydrocarbons undergo saturation, and sulfur, nitrogen, and other contaminant conversion. The conversion step forms a reaction slurry, or a hydrocarbon slurry with the biochemical liquor.

The enzymatic conversion reactions successively break the native, original, or solubilized, coal particles into smaller hydrocarbon molecules that remain in the reaction slurry. The enzymatic conversion reactions convert the high molecular weight molecular components of coal to lower molecular weight mixtures of hydrocarbon liquids and hydrocarbon gases.

During conversion, certain waste products, contaminants, and potential pollutants are removed from the process. In certain instances, the removal of these products is mediated by a third enzyme added to the reaction slurry. The third enzyme, or third enzyme solution, reacts with the products of catalytic conversion to liberate sulfur from the hydrocarbon complexes and form a variety of simpler sulfur-containing compounds, which are soluble in the reaction slurry. The soluble sulfur-containing compounds may be filtered from the reaction slurry and processed for other products.

Additionally, in order to remove other waste products, contaminants, and potential pollutants, a fourth enzyme may be added to the reaction slurry. In certain instances, any number of waste removal enzymes may be used to specifically eliminate, sequester, or cleave the unwanted compounds. In certain embodiments, the fourth enzyme solution reacts with the products of catalytic conversion to liberate nitrogen and form a variety of simpler nitrogen-containing compounds, which are soluble in reaction slurry.

The processed wastes may comprise gases solubilized in the reaction slurry. Gases may comprise nitrogen, oxides of nitrogen, sulfur, oxides of sulfur, carbon monoxide, carbon dioxide, and other gases without limitation. Certain waste products are used for further processes, such as syngas production, or catalyzed synthesis of liquid fuels. Further, enzymatically-catalyzed reactions convert the complex sulfur and nitrogen compounds found in coal to simpler forms that are removed during product separation.

As understood by one skilled in the art, the reaction properties such as temperature, pressure, pH and residence time are differentially monitored, and controlled for maximized production. In certain instances, the reaction properties are controlled to obtain a distribution of hydrocarbon molecular weights in the product stream. Further, as the reaction slurry comprises the biochemical liquor, altering the conditions may optimize conversion.

As discussed hereinabove, the biochemical liquor comprises any number of enzymes. As understood by one skilled in the art, each enzyme has preferred conditions for efficient catalysis. As such, cycling the reaction conditions, such as temperature and pressure, is envisioned to maximize the efficiency of any portion of the process, or the action of any portion of the enzymes. In other embodiments, the conversion step consists of separate reaction vessels for the solubilization, catalytic cracking, and nitrogen and sulfur conversion reactions. Such an arrangement permits different operating conditions to be used in each vessel, such as temperature and individual reactor recycle rates, to optimize the enzyme-catalyzed reactions.

Product Separation.

Following conversion, the hydrocarbon mixture is sent into settling tanks. In embodiments, the settling tank may be any vessel configured for separating the hydrocarbon liquid from the aqueous coal slurry. In certain instances, the settling tank may comprise a dynamic settler, wherein a constant low volume, or slow velocity, stream of the reaction slurry is introduced to separate the aqueous and hydrocarbon phases. Alternatively, the settling tank comprises a static settler, where the aqueous phase coal slurry settles from the lighter hydrocarbons by virtue of gravity. In certain embodiments, the remaining sulfur and nitrogen compounds distribute to the water phase. The hydrocarbon phase is separated by drawing off the lighter hydrocarbon layer from the denser aqueous layer. Alternatively, a conduit withdraws the aqueous phase from the bottom of the tank.

Product Enrichment.

The hydrocarbon layer, which already contains gasoline, kerosene, diesel, and fuel oils is sent to Stage II where it is further upgraded by converting the lower-valued fractions, naphtha, diesel, fuel oils, waxes, and the like to higher-valued fractions such as gasoline or kerosene. In embodiments, the product enrichment may comprise enzymatic conversion, molecular photofragmentation, conversion, and enzyme assisted molecular photo-fragmentation conversion. In certain instances, the product enrichment comprises a fifth enzyme, or fifth enzyme solution introduced to the hydrocarbon products from the separation step. Following enrichment, the hydrocarbon mixture is separated into final products by conventional distillation.

Ex-Situ Processing.

Figure 2:
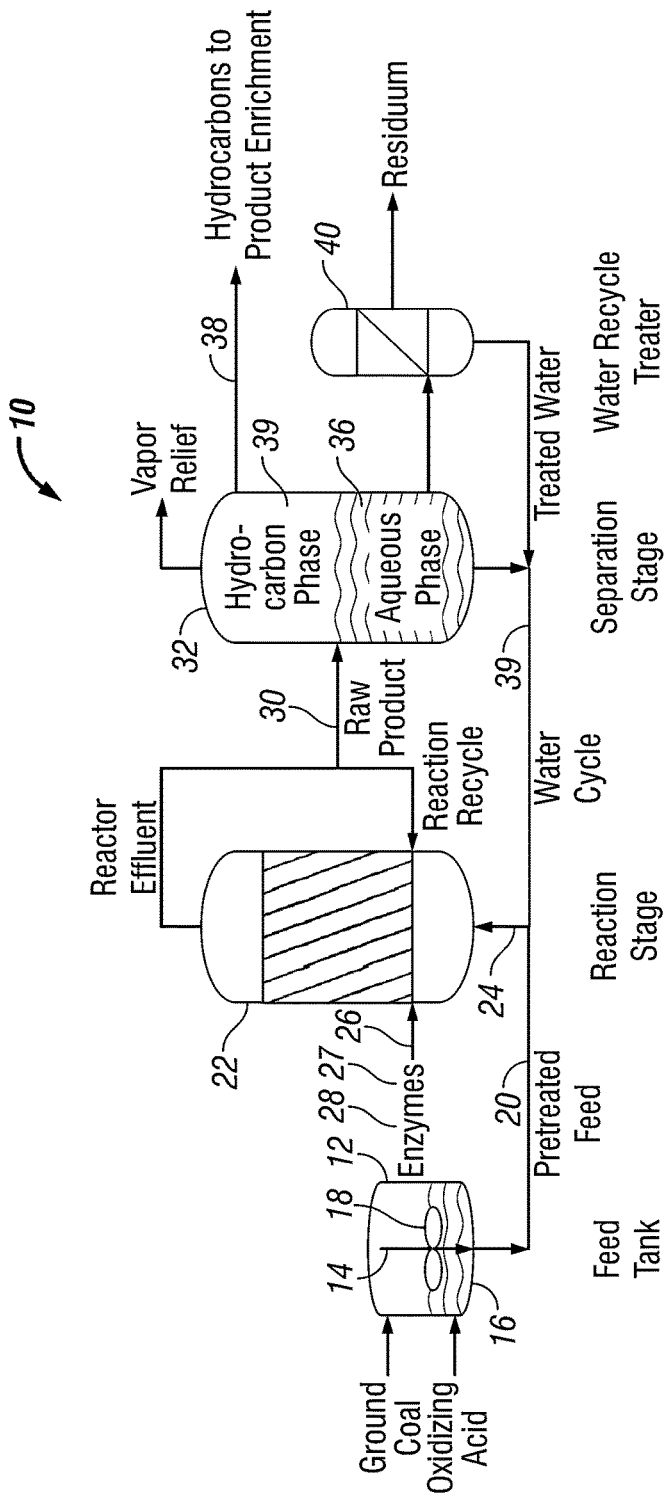
FIG. 2 illustrates one embodiment of an ex-situ process for converting coal to liquid.

FIG. 2 illustrates an embodiment of processing of ex-situ coal feedstocks continuously, or an EX-system 10. In the EX-system 10, pretreatment, conversion, and product processes are designed to be in fluid communication. In EX-system 10, the coal is first ground into small particles by mechanical means 12. As previously described, the mechanical means 12 creates a particulate product stream 14. The particulate product stream is introduced to chemical treatment system 16, comprising, for example, a weak acid solution. In certain instances, mechanical means 12 and chemical treatment system 16 may comprise a single vessel, or single processing facility. The coal and acid solution form coal slurry where the coal undergoes pre-oxidation. The extent of the pre-oxidation is determined by the residence time of the slurry in the chemical treatment system 16.

Further, in combined embodiments, the oxidation of the coal in the coal slurry may be controlled, at least in part, by the degree of agitation provided by mixers 18.

The slurry product stream 20 is then pumped out of the feed tank and into a reactor stage 22. The reactor stage 22 comprises the solubilization reaction. In certain instances, the first enzyme stream 24, with enzymes selected for solubilizing the coal, is injected into slurry product stream 20. Alternatively, first enzyme stream 24 is injected directly into reactor stage 22. Without wishing to be limited by theory, it may be beneficial for first enzyme stream 24 to be introduced to slurry stream 20 prior to introduction to reactor stage 22.

Reactor stage 22 comprises the enzyme mediated catalytic conversion reaction. Second enzyme stream 26 is injected into reactor stage 22. The enzymes react catalytically, convert the large hydrocarbon molecules, and produce product stream 30. Further, third enzyme stream 27 to convert sulfur compounds and fourth enzyme stream 28 to convert the nitrogen compounds are added to reactor stage 22. The third enzyme stream 27 and fourth enzyme stream 28 convert the respective contaminants found in the coal slurry 20 into simpler, water-soluble forms. Reactor stage effluent 23 is continuously split between a recycle stream 25, which is pumped back into the reactor stage 22, and a product stream 30.

In other embodiments, the reaction stage 22 consists of separate reaction vessels for the solubilization, catalytic conversion, and nitrogen and sulfur conversion reactions. A multiple reactor arrangement permits different operating conditions to be used in each vessel, such as temperature and individual reactor recycle rates, to optimize the different suites of reactions.

The product stream 30 is pumped into the separation stage 32. Separation stage 32 may comprise gas vent 33 for withdrawing the gases and volatile compounds released during separation. In certain instances, gas vent 33 vents some gases that were dissolved in product stream 30. The separation stage 32 comprises the step where the aqueous phase 36 settles out under the hydrocarbon phase 34. Separation stage 32 comprises a settler, or settling vessel. Alternatively, separation stage is a filter or other apparatus to separate aqueous and hydrocarbon phases from product stream 30. Separation stage 32 comprises a continuous flow, oil separation vessel. The aqueous phase 36 is withdrawn from separation stage 32 and routed via recycle stream 39 to the reactor stage 22. The recycle stream comprises a wastewater treatment system. The treatment system comprises any system configured as a sour water treatment, configured to remove residuum, as well as nitrogen and sulfur by-products. Treated water is then recycled back to the reactor section.

In certain instances, the hydrocarbon phase 34 may be withdrawn from the top of the settler as hydrocarbon stream 38 for enrichment and/or distillation to produce transportation fuels. The hydrocarbon stream 38 is pumped to a product enrichment stage.

In-Situ Processing

Figure 3:
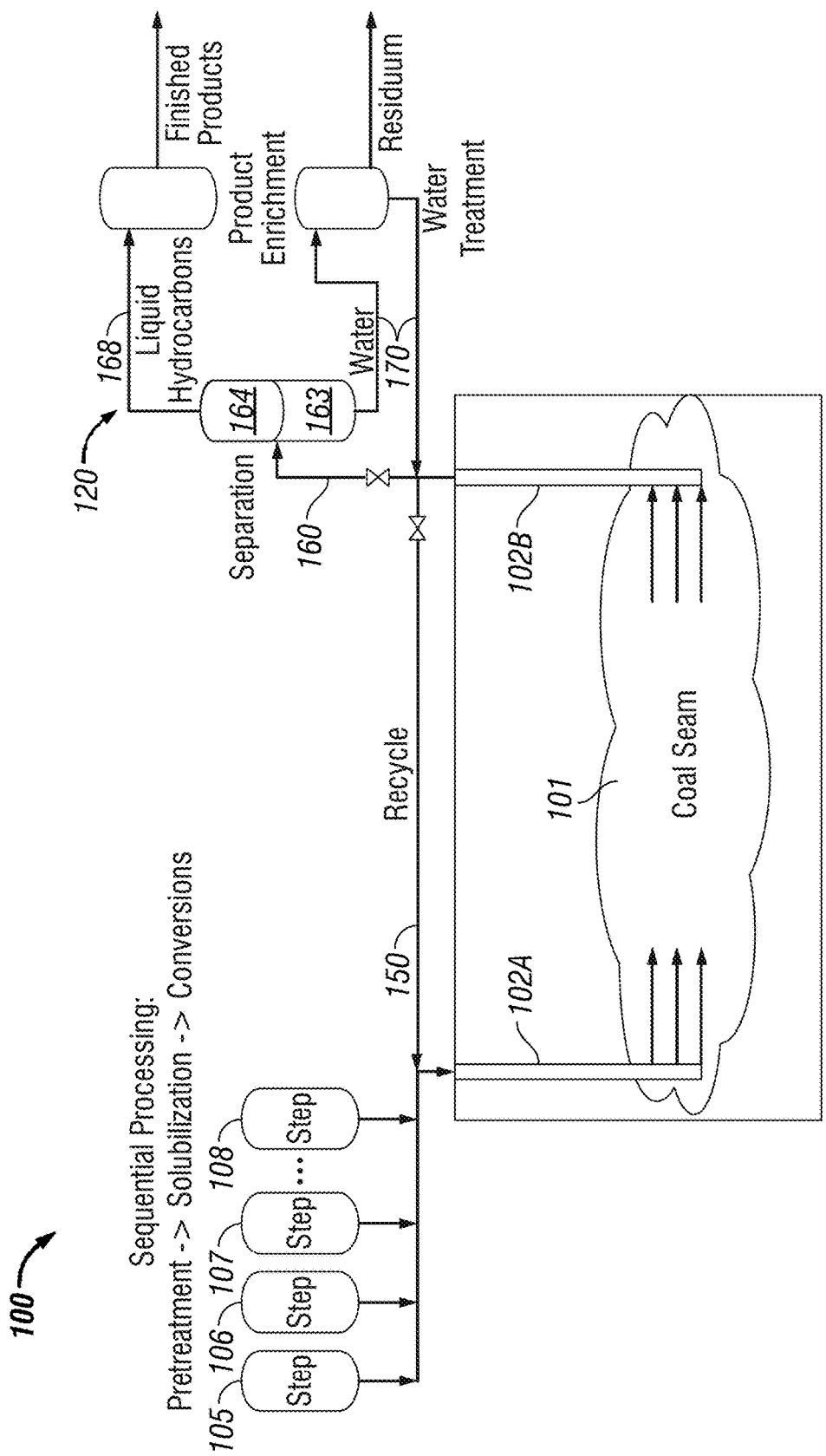
FIG. 3 illustrates one embodiment of an in-situ process for converting coal to liquid.

Another embodiment involves the continuous processing of in-situ coal, or IN-system 100, which is illustrated in FIG. 3. In this embodiment, the IN-system 100 comprises an abandoned, collapsed, inaccessible, or otherwise difficult to mine coal deposit, or underground coal seam 101. In embodiments, at least one well 102 is drilled into the coal seam 101. The wells 102 are generally configured for the transport of liquids and slurries between the underground coal seam 101 and the processing center 120. Further, the wells 102 may be configured for the continuous circulation of process fluids in and out of the underground coal seam 101. It can be envisioned that a plurality of wells 102 would improve product yield, processing time, and the general economics of the IN-system 101, without limitation.

The IN-system 100 process begins with the injection of steam in the well 102 conduits to induce fracturing of the underground coal seam 101. This fracturing step 105 is configured to break the coal seam into particulates, coal gravel, or the like. In certain instances, using high-pressure steam is according to conventional practices of the underground coal mining industry.

After the fracturing step 105 is complete, the high-pressure steam is withdrawn. The oxidation step 106 comprises injecting an acid solution to pre-oxidize the fractured coal. In embodiments, the acid solution is recycled continuously to form a circulating process stream 150, such that the acid is pumped into well 102A at one side of the seam, pumped out of well 102B on the other side of the seam. To complete the cycle, the acid solution is transported back and pumped into the first well 102A. The circulating process stream 150 may be repeated until the desired level of pre-oxidation is achieved.

As described above, the solubilization step 107 may comprise the introduction of the first enzyme solution into the underground coal seam 101. The first enzyme solution is introduced into the circulating process stream 150 to solubilize the exposed coal into the circulating process solution.

Once an adequate level of soluble coal is achieved, to create coal slurry in the circulating process stream 150, the additional enzymes are added either sequentially or simultaneously. In certain instances, the second enzyme 106, third enzyme 107, and fourth enzyme 108 solutions are added to the circulating stream 150. As described herein above, the second enzyme stream 106 is selected to catalytically crack the hydrocarbons. The third enzyme 107 and fourth enzyme 108 solutions are selected to remove sulfur and nitrogen-containing compounds and/or waste products from the circulating process stream 150. In embodiments, further enzyme streams may be injected into circulating process stream 150 to optimize the solubilization and conversion of the coal.

A portion of the circulating process stream 150 is then split and taken as a raw product stream 160 and sent to a processing stage 120. The processing stage 120 is similar to the one used in ex-situ embodiments of the process described above. Separation vessel 162 comprises the step where the aqueous phase 163 settles out under the hydrocarbon phase 164. Separation vessel 162 comprises a settler or settling vessel. The aqueous phase 163 is withdrawn from separation vessel 162 and routed via recycle stream 170 to the circulating process stream 150. The recycle stream 170 comprises a wastewater treatment system. The treatment system comprises any system configured for sour water treatment, configured to remove residuum, as well as nitrogen and sulfur by-products. In certain instances, the hydrocarbon phase 164 may be withdrawn from the top of the settler as hydrocarbon stream 168 for enrichment and/or distillation to produce transportation fuels. The hydrocarbon stream 38 is pumped to a product enrichment stage.

Mutagenesis.

Figure 4:
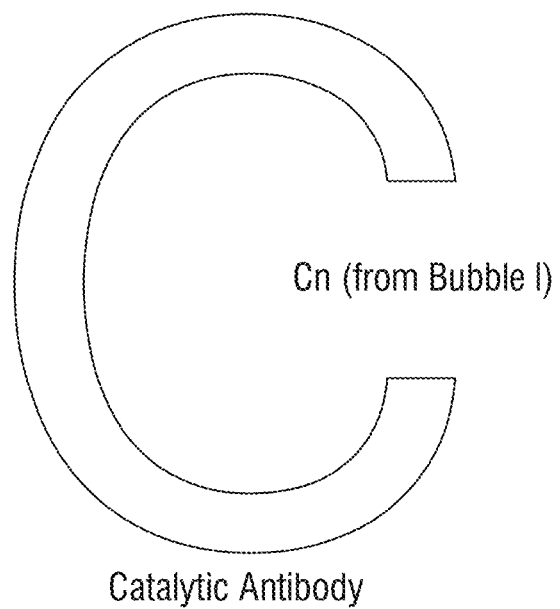
FIG. 4 illustrates a representative diagram of a catalytic antibody.
Figure 5:
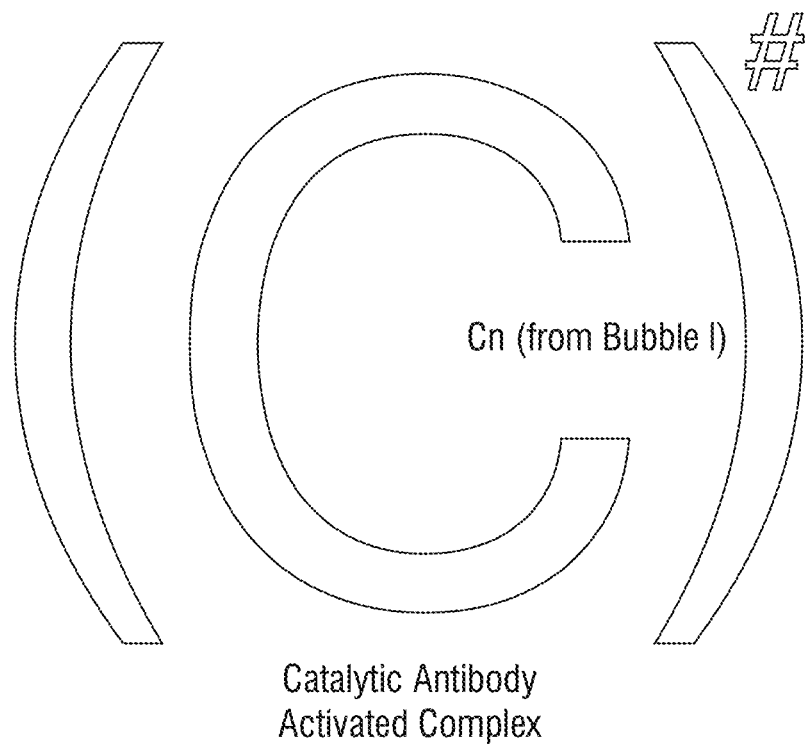
FIG. 5 illustrates a representative diagram of an activated catalytic antibody.
Figure 7:
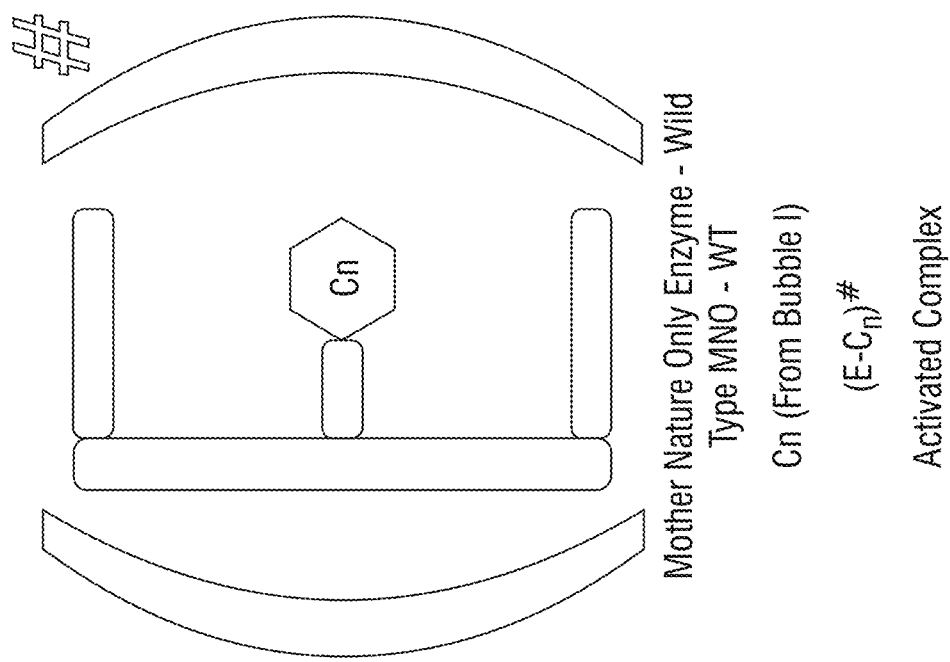
FIG. 7 illustrates a representative diagram of an activated enzyme complex.
Figure 6:
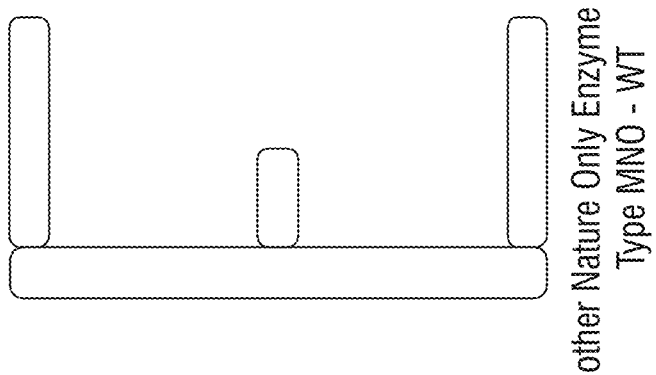
FIG. 6 illustrates a representative diagram of a wild type enzyme.

Methods used to produce suitable enzymes for implementation in Stage II for fuel upgrade include using catalytic antibodies. As illustrated in FIG. 4, biological enzymes are identified for the catalytic processes desired. In certain instances, the biological enzymes are derived from the microorganisms discussed herein above. In further embodiments, the enzymes comprise Mother Nature only (MNO) enzymes. MNO enzymes are the phenotypic expressions of unmodified genetic sequences within the microorganisms. Alternatively, MNO enzymes are wild-type enzymes. In further instances, illustrated in FIG. 5, the MNO enzymes are selected from those that comprise an activated enzyme. In certain instances, the activated enzyme screening is conducted by an antibody assay. Alternatively, any suitable screening method may comprise any suitable protocol to identify the wild type MNO enzymes, as further illustrated in FIGS. 6 and 7.

Figure 9:
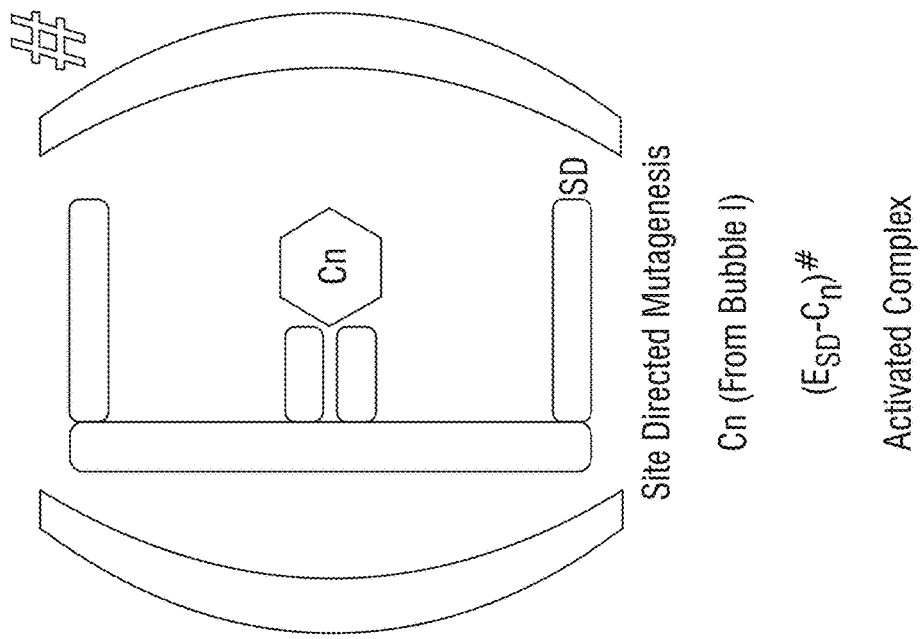
FIG. 9 illustrates a representative diagram of site directed mutagenesis of an activated enzyme complex.
Figure 8:
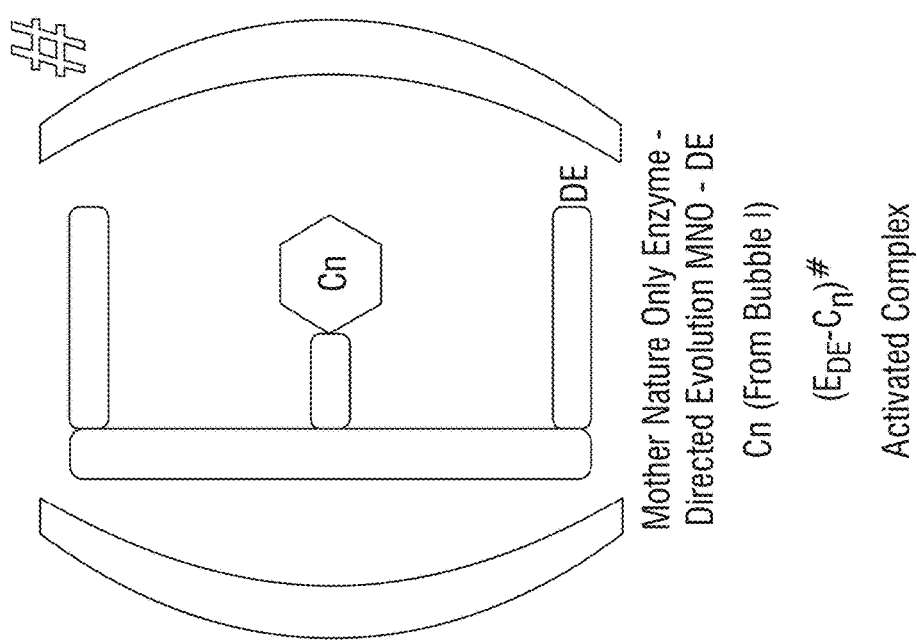
FIG. 8 illustrates a representative diagram of a directed evolution of an activated enzyme complex.

The MNOs selected are formed by directed evolution, as illustrated in FIG. 8. The selected MNOs are subject to site-directed and random mutagenesis throughout the enzyme, not solely restricted to the active site. In certain instances, the enzymes are also subject to mutagenesis at allosteric sites, and at sites remote from active and/or allosteric sites. The mutagenesis at multiple sites comprises a means to both promote and restrict potential products as illustrated in FIGS. 9 and 10. In certain instances, the mutagenesis includes active site chemical redesign as shown in FIG. 11. Preferably, the results include a rational design enzyme, or enzymatic structure.

The structure is synthesized, computationally designed, with motifs attached to enzyme scaffolds. As enzymes are rather large molecules, having hundreds of amino acids, tens of kilo Daltons (Kds), and thousands of cubic angstroms, they may be considered spatially inefficient. In certain instance, large enzyme molecules comprise small active sites. Enzymatic reactive sites are quite small by comparison and the other folded amino acids serve as a scaffolding to create the reactive site volume. These "other" amino acids can be, relatively speaking, quite far from the active site of the enzyme as illustrated in FIG. 12. Additionally, the enzymes may include cofactor attachment site redesigns, shown in FIG. 13. In order to induce cofactor attachment site redesigns the implementation of site directed mutagenesis are repeated as discussed hereinabove, for example, paragraph 21.

Figure 14:
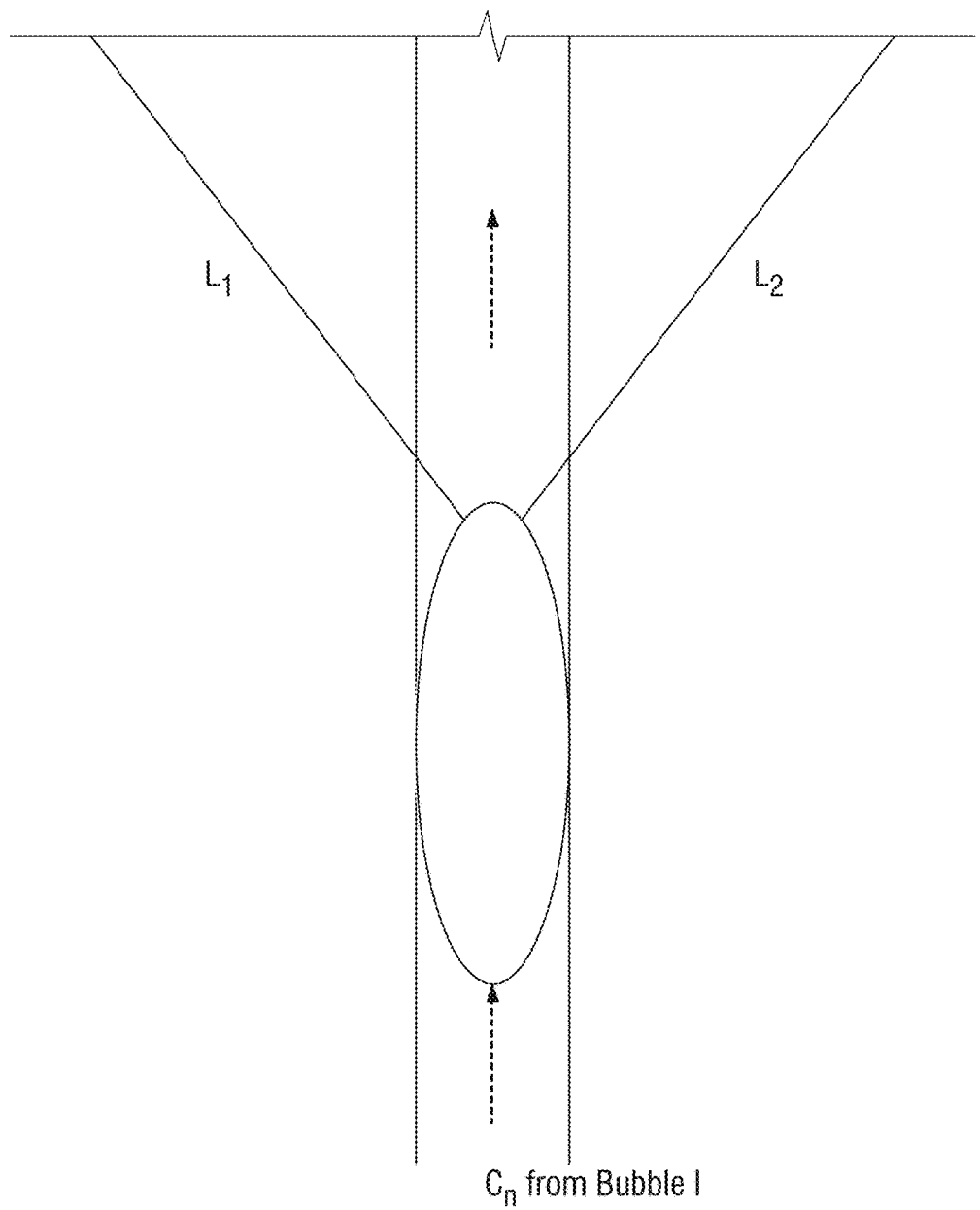
FIG. 14 illustrates a schematic of photofragmentation.
Figure 15:
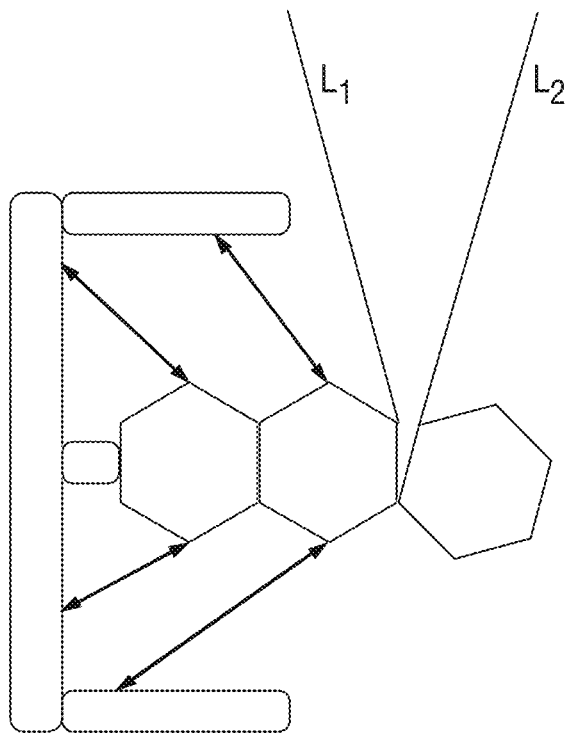
FIG. 15 illustrates a schematic of laser mediated photofragmentation.

As diagrammed in FIG. 14, a shaped IR femtosecond laser pulse may be impinged upon the enzymatic complex to induce reactant fragmentation. Further, it can be envisioned that any particular impingent radiation, known to one skilled in the art, may be capable of the same reactant fragmentation, without limitation. The laser pulse for directed fragmentation of reactants/conversion to products may aid the formation of reactant products. As understood by one skilled in the art, multiple fragmentation reactant products may be formed. In certain instances, the multiple fragmentation products may be advantageous for the formation of a range of reactant fragments. Alternatively, the shaped IR femtosecond laser pulses in conjunction with above mentioned enzyme techniques to assist in selective fragmentation of reactants at enzymatic active sites, allosteric sites, and sites remote from binding or allosteric sites as shown in FIG. 15. As understood by one skilled in the art, the bonding of the reactant, hydrocarbon, molecular to the enzyme reactive site may comprise a covalent, non-covalent, hydrogen, ionic, Van der Waals, or other bond, interaction, coupling, or association, without limitation. Further, the enzyme reactive site is configured to restrict the reactant molecule, and its range of movement. Further, the reactive site restricts internal degrees of freedom, to favorably target the femtosecond laser pulses to the preselected internal bond. In certain instances, the enzyme reactive site damps the internal degrees of freedom, such that internal vibrational rearrangement (IVR) is prevented, and the laser energy is focused to the preselected internal bond.

Conversion of Coal to Liquid Hydrocarbons.

In an embodiment, a process of converting coal to liquid hydrocarbons comprises mechanical pretreatment and/or chemical pretreatment, solubilization, and conversion (from coal to liquid hydrocarbons). Mechanical pretreatment includes hammer mill grinding or jet mill grinding. In some cases, jet mill grinding is able to grind coal into particles with sizes of 5 µm or less. For example, a Fluid Energy Model 0101 JET-O-MIZER-630 size reduction mill may be used.

In an embodiment, solubilization and conversion are performed on various pretreated coal. In some cases, coal is pretreated by an enzymatic process, for example, using extracellular Laccase and Manganese Peroxidase (MnP). In some cases, coal is pretreated by a chemical process, for example, using Ammonium Tartrate and Manganese Peroxidase. In some cases, coal is pretreated by an enzymatic process, for example, using live organisms *Phanerochaete chrysosporium*.

EXAMPLE

Overview.

Coal is decomposed with three different approaches (1) an enzymatic process—using extracellular Laccase and Manganese Peroxidase (MnP); (2) a chemical process—using Ammonium Tartrate and Manganese Peroxidase; and (3) an enzymatic process—using live organisms *Phanerochaete chrysosporium*. Spectral analysis was used to determine how effective each of these methods is in decomposing bituminous coal. After analysis of the results and other considerations, such as cost and environmental impacts, it was determined that the enzymatic approaches, as opposed to the chemical approaches using chelators, were more effective in decomposing coal. The results from the laccase/MnP experiments and *Phanerochaete chrysosporium* experiments are presented and compared.

Spectra from both enzymatic methods show absorption peaks in the 240 nm to 300 nm region. These peaks correspond to aromatic intermediates formed when breaking down the coal structure. The peaks then decrease in absorbance over time, corresponding to the consumption of aromatic intermediates as they undergo ring cleavage. The results show that this process happens within 1 hour when using extracellular enzymes, but takes several days when using live organisms. In addition, live organisms require specific culture conditions, control of contaminants and fungicides in order to effectively produce extracellular enzymes that degrade coal. Therefore, when comparing the two enzymatic methods, results show that the process of using extracellular lignin degrading enzymes, such as laccase and manganese peroxidase, appears to be a more efficient method of decomposing bituminous coal.

Mechanical Pretreatment.

The mechanical pretreatment process involves grinding the coal particles down to a smaller size before chemical pretreatment and experimentation. This process provides an increased surface area for both the chemical pretreatment of coal as well as a greater surface area for the subsequent enzymatic conversion of coal to liquid hydrocarbons.

Bituminous coal was used, Lower Kittanning Seam, high vol—No. 5, from Rosebud Mining Company, Kittanning, Pa.

In Q1, three different coal grinds were used: 1 mm, 400 µm and 40 µm sized particles. All three of these grinds were performed using hammer mill grinding. The 1 mm particles came from Rosebud Coal, Kittanning, Pa. The 400 µm and 40 µm particles came from Pulva Corporation, Valencia, Pa. (although the starting material for the micron sized grinds was also 1 mm Rosebud coal). The mechanical pretreatment process in Q2 was changed from hammer mill grinding to jet mill grinding. This was performed by Fluid Energy, Inc., Telford, Pa. The equipment used was a JET-O-MIZER Size Reduction System. The actual grinding was done under sealed conditions, excluding any oxygen or air. This was done for safety reasons, to guard against any spontaneous ignition or explosions. Further mechanical grinding work was performed in Q3 using a Fluid Energy reduction mill (e.g., Fluid Energy Model 0101 JET-O-MIZER 630 size reduction mill). The Fluid Energy Model 0101 JET-O-MIZER 630 size reduction mill takes 3 mm sized coal particles for input. This particle size is readily available from coal producers. At a specific energy consumption of roughly 1,000 kWh/t, using steam as the motive gas, mean particle sizes of less than 5 microns are obtained.

Figure 16:
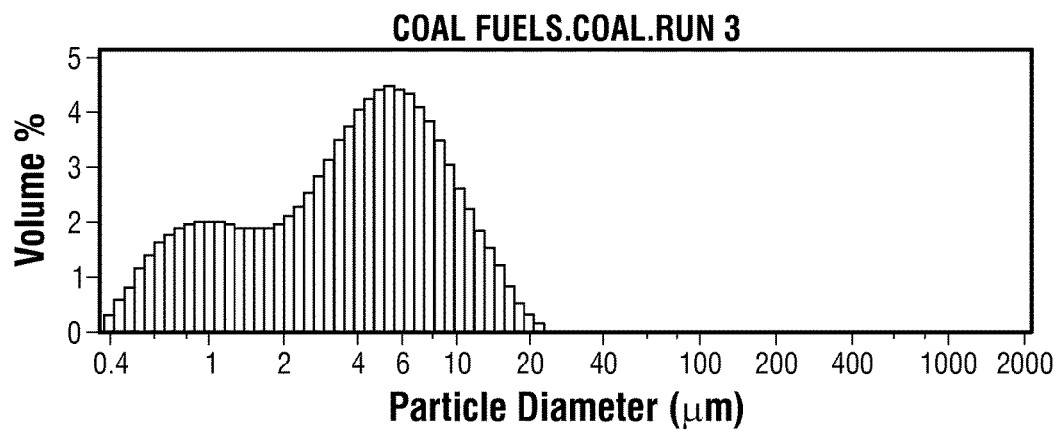
FIG. 16 shows the results from the mechanical grinding run performed on the Fluid Energy Model 0101 JET-O-MIZER 630 size reduction mill.

Results and Discussion. FIG. 16 shows the results from the mechanical grinding run performed on the Fluid Energy Model 0101 JET-O-MIZER 630 size reduction mill. As seen this figure, 25% of the particles are less than 1.7 microns and 50% are less than 4 microns. The Sauter mean diameter, D(3,2), is only 2.128 microns and the specific surface area is over 28,000 cm2 per cm3. These small particle sizes result in an increased surface area, which means an increase in the number of functional groups of coal that become exposed to enzymes during the solubilization and hydrocarbon conversion process (see Table 1 below).

Model 0101 JET-O-MIZER CFS Test Mill is abbreviated as "CFS Mill", which was fitted with a steam interface to the grinder. The dimensions of the CFS Mill are roughly 7×6×3 feet. Behind the control panel on the right are 2 heaters for steam. A coal hopper feeds coal into the grinding section (jacketed cube to left of hopper). Ground coal product is fed into a container behind the jacketed grinder.

TABLE 1

COULTER ® LS Particle Size Analyzer 13:25
Fluid Energy Ajet

| File name: | CL 10327.303 | Group ID: | CL 10027 |
|---|---|---|---|
| Sample ID: | COAL FUELS; COAL; RUN 3 | Run number: | 79 |
| Operator: | YP | | |
| Comments: | PSI-100 N2; F/r-3M-R JCM0101 | | |
| Optical model: | Fraunhofer | | |
| LS 230 | Small Volume Module | | |
| Start Time: | 13:21 | Run length: | 60 seconds |
| Observation: | 7% | | |
| PIDS obocur: | 54% | | |
| Fluid: | 2-Propanol | | |
| Software: | 2.09 | Firmware | 2.02 2.02 |

Figure 17:
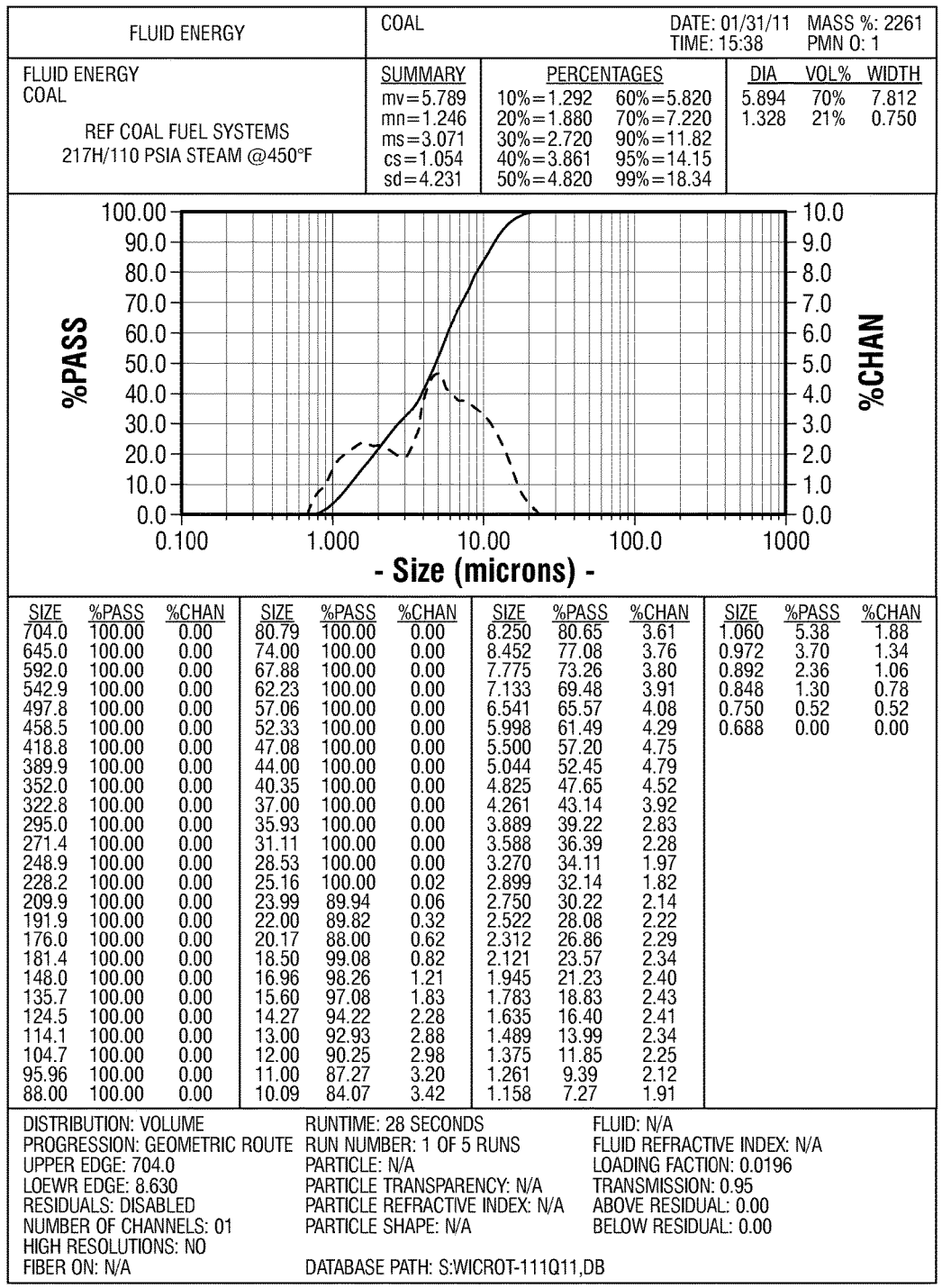
FIG. 17 shows the results obtained from the completed CFS Mill.

FIG. 17 shows the final results obtained from the completed CFS Mill. The coal product statistics are taken from a liquid product. These results come from a MICROTRAC Standard Range Analyzer (SRA 150). As seen in FIG. 17, the grinding on the CFS Mill is done at a feed rate of coal of 27 pounds per hour. The motive steam is at 450 0F and 110 PSIG. The coal particle range is roughly from 0.5 microns to 25 microns. The mean value is 5.769 microns.

In addition to the statistical results, the coal from the CFS Mill was examined under a microscope. In the following micrographs, a number of features of the coal grind and particles are evident.

Figure 18A:
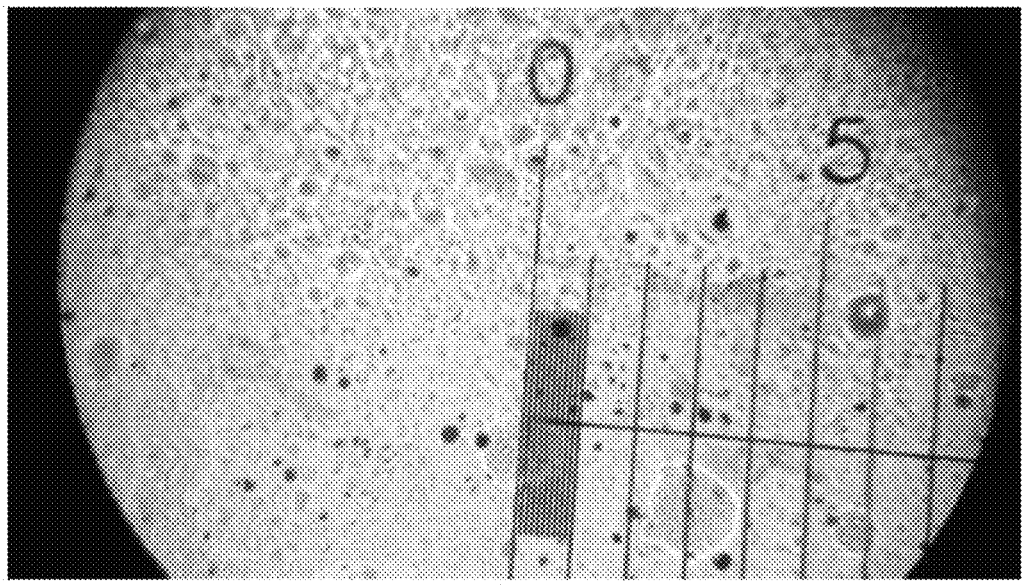
FIGS. 18A-18C are micrographs of product in water; 18A at magnification of 125×; 18B at magnification of 430×; 18C at magnification of 1000×.

FIG. 18A is a micrograph of product in water. The magnification is 125×. The graticuled microscope slide is divided in tenths (0.1 mm) of a millimeter, as can be seen in the 0 to 0.5 divisions. The 0.1 mm divisions are further subdivided again into tenths (0.01 mm) in the 0.0 to 0.1 mm subdivision. The 0.01 mm divisions look like "guitar strings." The large particle in the middle of the "guitar strings" is about 30 microns in diameter. It is the largest particle in the visible field. Some particles are much, much smaller as can be seen in the next 2 micrographs.

Figure 18B:
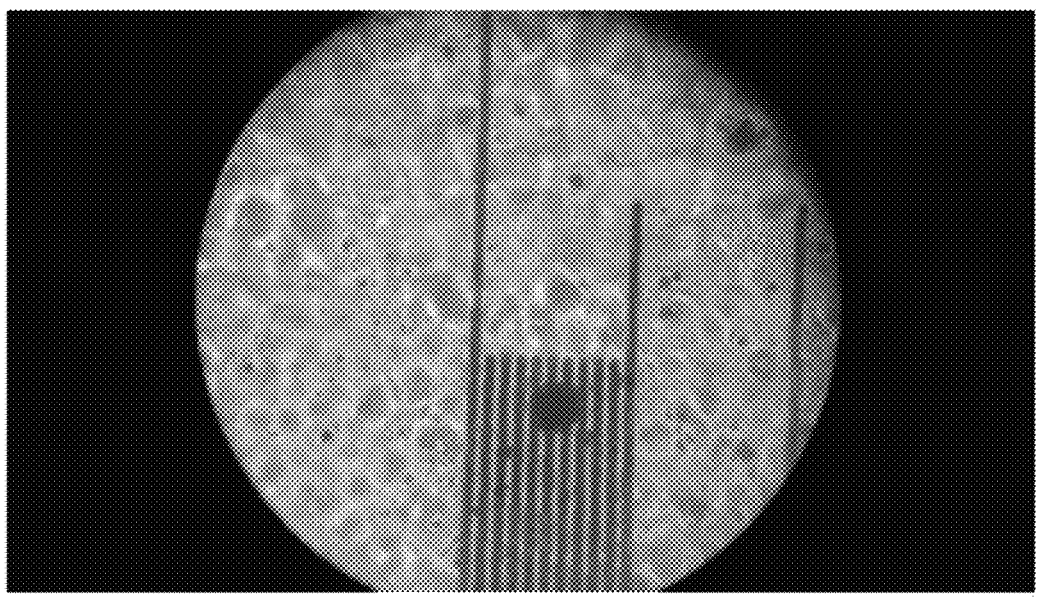
Figure 18C:
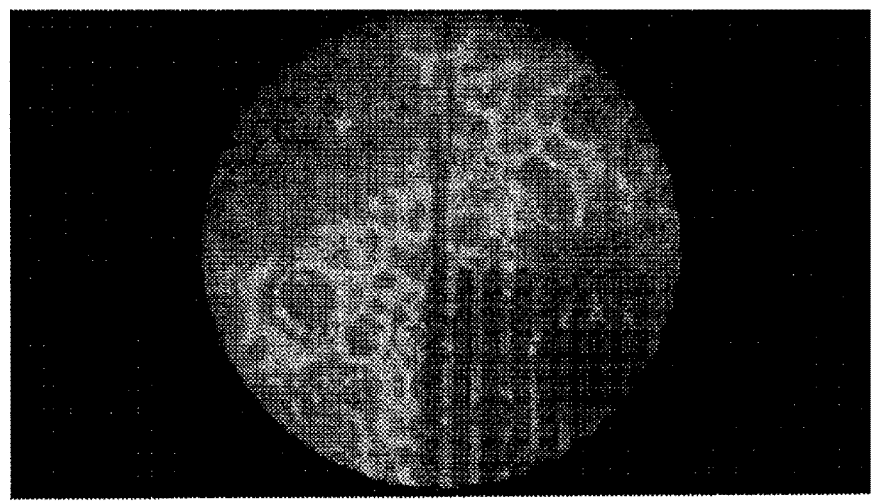

FIG. 18B is at magnification 430×. The guitar strings are divisions of 10-5 m. As can be seen between strings and around the central field, there are particles 0.1 of the string divisions or about 1 micron. FIG. 18C is a micrograph of the same central field as FIGS. 18A-18B. The magnification is 1,000×. At this magnification, please note the orange circled particle. It is about 10 microns in diameter. Naturally there is diffraction of visible light around particles of this size. However, note that there appears to be some transparency through the middle of the particle. This phenomenon is also apparent throughout other particles on this slide as well as on other, not shown, micrographs.

A few different approaches for mechanical pretreatment were used in this example. Ultimately, it was decided to use jet mill grinding (as opposed to hammer mill grinding) which is able to grind the coal particles to 5µ size or smaller. As seen in the results, a Fluid Energy Model 0101 JET-O-MIZER 630 size reduction mill is able to perform to the required specifications and grind the coal particles to sizes 5 µm or less. The coal grinding process is extremely important because at particle sizes of 5 µm or less, the dramatically increased surface area provides additional exposure of functional groups that then become exposed to enzymes. This is beneficial because increased reaction rates and product volumes are highly dependent upon access, or exposure, to these functional groups.

The particle sizes and dispersion of coal particles borders on the definition of "solubility." The particles are on the order of 800-1,200 benzene rings. These are quite favorable sizes to be "fed" to the series of enzymes to produce liquid fuels.

Solubilization and Conversion.

Bituminous coal was used (Lower Kittanning Seam, high vol—No. 5, from Rosebud Mining Company, Kittanning, Pa.). A mechanical grinder was used to grind the coal prior to running the experiments. As mentioned in the mechanical pretreatment section, a few different particle sizes were used but most of the experiments were conducted using about 5 µm sized coal particles. The results analyzed are from the experiments using the 5 µm sized coal particles.

Chemical pretreatment is used to "weather" or oxidize the coal, which in turn assists in the solubility of the coal in the enzymatic conversion process. Several different pretreatments were used in the experiments, including: hydrogen peroxide, H2O2 (3% pH 5, 15% pH 4.5, and 30% pH 4), PBS Mine H2O (Somerset, Pa. pH 2.2), nitric acid, HNO3 (pH 1, pH 2, pH 3, pH 4, and 15M), distilled H2O, and preheated coal, in which the 5 µm coal was preheated at a temperature of 120° C. for approximately 36 hours. All of the pretreated samples were dried before the coal was used for the experiments.

In addition to conducting experiments with the different types of pretreated coal, experiments were also conducted with untreated coal. The results from pretreated coal experiments were analyzed to determine the most effective pretreatments. From these results, it was determined that the most effective pretreatments were hydrogen peroxide (3%, 15%, and 30%), heated coal, mine water, and nitric acid. The results from the experiments using these specific pretreated coal samples are discussed.

Enzymatic Approach: Laccase and Manganese Peroxidase

Enzymatic experiments in this example were conducted using Laccase from *Trametes versicolor* and Manganese Peroxidase (MnP) from *Phanerochaete chrysosporium*, both purchased from Sigma-Aldrich. Laccase and MnP are extracellular enzymes produced by white rot fungi. They are considered to be two of the major groups of ligninolytic enzymes and are capable of efficiently degrading lignin. Laccase was used for the first step of the process, enzymatic solubilization, and MnP was used in the second step of the process, hydrocarbon conversion. The detailed experimental procedure for this approach is shown below.

Laccase and MnP Procedure

Step 1: Laccase
  Solutions:
  Laccase buffer—100 mM citric acid—100 mM sodium phosphate buffer, pH 4.5
  Laccase solution—laccase (*T. versicolor*) was dissolved in laccase buffer
  Procedure
  1) 0.1 g of dried, pretreated coal was combined with 3 ml of laccase buffer in a test tube
  2) 2 ml of laccase solution added to each test tube containing the coal and laccase buffer
  3) Each test tube was shaken on a Shaker Lab Line Orbital Shaker overnight
  4) Products from experiments were measured using the Genesys 10 UV-VIS spectrophotometer (range 190 nm-1100 nm), purchased from Fisher Scientific. The product concentrations (number of drops) measured in the spectrophotometer were adjusted so that the absorption intensities were relatively the same.

Step 2: Manganese Peroxidase (MnP)
  Solutions
  MnP Buffer—160 mM malonic acid solution, pH 4.5
  MnP solution—MnP oxidizer solution was mixed in MnP buffer to form the Mnmalonate complex (complex described in assay procedure)
  Procedure
  1) 2.5 mL of MnP solution was added to spectrophotometer cuvette
  2) Few drops of each product from laccase experiments (product from Step 1) were added to cuvette to conduct hydrocarbon conversion. The concentrations (number of drops) were adjusted so that the absorption intensities were relatively the same.
  3) Products from experiments were measured immediately and then every 15 minutes (up to 1 hour) using the Genesys 10 UV-VIS spectrophotometer (range 190 nm-1100 nm), purchased from Fisher Scientific Chemical Approach: Chelators A chemical approach using chelators was also used in this example. Chelators act to remove complex ions from the coal structure to solubilize coal. Three different chelators were used, however, ammonium tartrate appeared to be the most effective chelator. For the experiments, ammonium tartrate was used in the solubilization step of the process and MnP was then used in the hydrocarbon conversion step of the process. A more detailed procedure for this approach is shown below.

Chelator Procedure

Step 1: Ammonium Tartrate
  Solution
  Chelator Solution—1.00 g of ammonium tartrate was mixed with 250 ml of H2O Procedure
  1) Coal—0.10 g of each pretreated dried coal sample was used for each experiment
  2) 0.1 g of coal combined with 10 ml of chelator solution in each test tube
  3) Each test tube was shaken on a Shaker Lab Line Orbital Shaker overnight
  4) Products from experiments were measured using the Genesys 10 UV-VIS spectrophotometer (range 190 nm-1100 nm), purchased from Fisher Scientific. The product concentrations (number of drops) measured in the spectrophotometer were adjusted so that the absorption intensities were relatively the same.

Step 2: Manganese Peroxidase
  Solutions
  MnP Buffer—160 mM malonic acid solution, pH 4.5
  MnP solution—MnP oxidizer solution was mixed in MnP buffer to form the Mnmalonate complex (complex described in assay procedure)
  Procedure
  1) 2.5 mL of MnP solution was added to spectrophotometer cuvette
  2) Few drops of each product from tartrate experiments (product from Step 1) were added to cuvette to conduct hydrocarbon conversion. The concentrations (number of drops) were adjusted so that the absorption intensities were relatively the same.
  3) Products from experiments were measured immediately and then every 15 minutes (up to 1 hour) using the Genesys 10 UV-VIS spectrophotometer (range 190 nm-1100 nm), purchased from Fisher Scientific Enzymatic Approach: *Phanerochaete Chrysosporium*

In addition to using extracellular enzymes, experiments were conducting using live organisms known to produce lignin degrading enzymes. These experiments were designed to provide an environment for the live organism to excrete such extracellular enzymes to degrade pretreated coal. The organism used, *Phanerochaete chrysosporium* (*P. chrysosporium*), is a white rot fungi which excretes extracellular enzymes to degrade lignin. This organism was purchased from ATCC (ATCC #24725). Two different growth media were used to grow the *P. chrysosporium*: Potato Dextrose (PD) and Sabouraud Dextrose (SD). A more detailed experimental procedure for this approach is shown below.

*P. Chrysosporium* Procedure
  1) 0.2 g of dried, pretreated coal was weighed and placed into a 50 ml Erlenmeyer flask
  2) 30 ml of growth media broth (inoculated with *P. chrysosporium*) was added to the coal in the flasks
  3) Each flask was shaken on a Shaker Lab Line Orbital Shaker constantly for 14 days
  4) Samples were taken from each flask after the first 2 hours for an initial reading, as well as once a day on Days 1-7, Day 10, and Day 14. These samples were measured using the Genesys 10 UV-VIS spectrophotometer (range 190 nm-1100 nm), purchased from Fisher Scientific.

Results.

As previously described, three different approaches were taken when conducting the solubilization and conversion experiments: (1) laccase and MnP, (2) ammonium tartrate and MnP, and (3) live *P. Chrysosporium* using two different growth media. The first two approaches included a solubilization step, using both enzymes and chelators, to initially decompose the coal structure; the decomposed coal is passed to a hydrocarbon conversion step, using additional enzymes, to further crack the hydrocarbon molecules into smaller hydrocarbon molecules. In the live organism approach, *P. Chrysosporium* was used to excrete a number of extracellular enzymes to both decompose and then further crack the coal structure.

After experimentation with enzymes and chelators in the second and third quarters, it was determined that the enzymatic approach was more effective in degrading bituminous coal than the chemical (chelator) approach. In addition, chelators are expensive and pose potentially adverse, environmental impacts. From these experimental results and environmental considerations, it was determined that the chelator approach was not optimal.

The experiments with live *P. Chrysosporium* were conducted using different types of growth media. Results from these experiments showed that the optimal growth conditions were the PD growth medium and the SD growth medium, both with the least amount of peptone added.

Successful results of coal degradation were obtained from both the enzymatic approach (laccase and MnP) and live organism approach (*P. Chrysosporium*). Therefore, only the spectral results from these approaches are presented and analyzed. FIGS. 19A through 22C show the results from these experiments.

Each curve shows wavelength (nm) vs. relative absorbance (A), where relative absorbance (A) is related to transmittance (T): A=log 10 (1/T). The legends on the graphs should be read left to right, showing the order in which samples were measured.

The results are divided into sections according to the type of pretreatment used. Only the spectral results from the most effective pretreatments are presented. These pretreatments are hydrogen peroxide (3%, 15%, and 30%), heated coal, mine water, and nitric acid (pH 1) pretreatments. After a comparison of these results the best overall approach for degradation of bituminous coal will be determined.

3% H2O2 Pretreated Coal

Figure 19A:
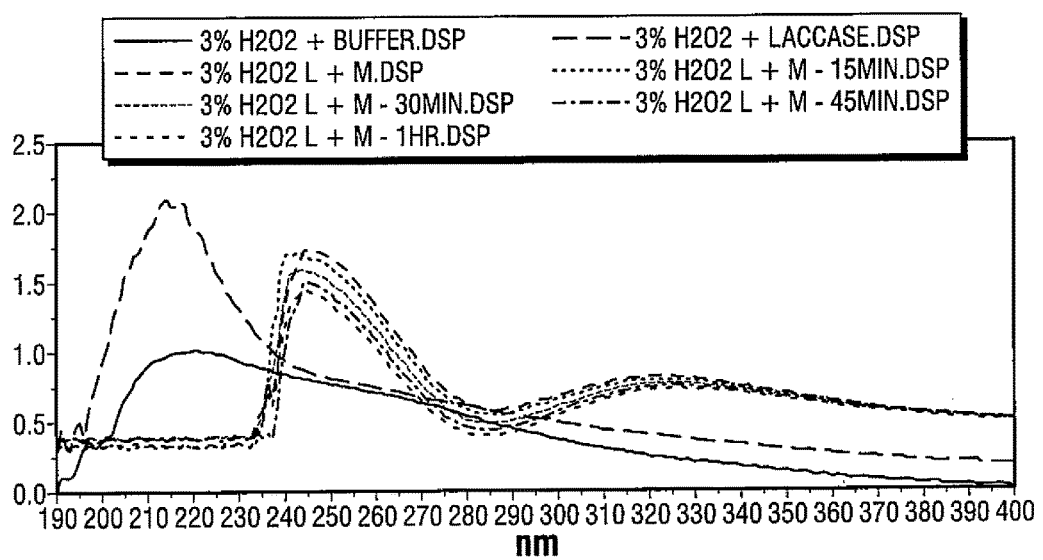
FIG. 19A illustrates the results from the 3% H2O2 pretreated coal in enzymatic solubilization and conversion.

FIG. 19A illustrates the results from the 3% H2O2, pretreated coal experiments using the laccase and MnP solutions. The spectrum for the pretreated coal in laccase buffer shows a peak around 215 nm and an absorbance of about 1.0 A (red curve). This spectrum can be compared to the spectrum of the pretreated coal in laccase solution, which shows a peak around 215 nm and an absorbance of about 2.0 A (blue curve).

These two spectra show that the 3% H2O2 pretreatment does have some effect on solubilizing the coal, but the laccase works to further oxidize and solubilize it. The spectra in FIG. 19A also illustrate a shift in peaks from 215 nm to about 244 nm and a decrease in absorbance from 2.0 A to 1.74 A, which occurs when the laccase product was added to the MnP solution (green curve—0 min). The absorbance (green curve—0 min) continues to decrease over time to about 1.45 A (pink curve—15 min, turquoise curve—30 min, yellow curve—45 min, gray curve—1 hr).

Figure 19B:
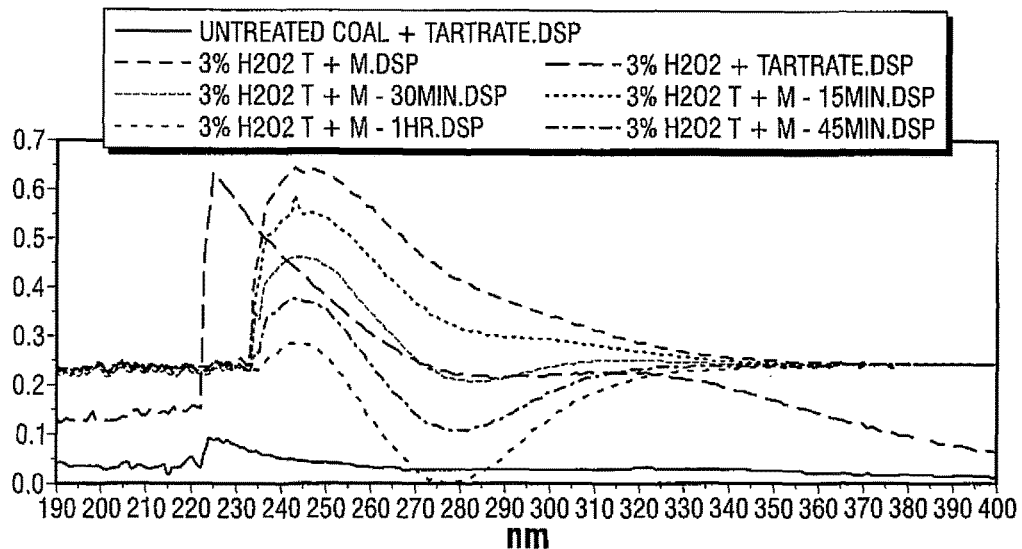
FIG. 19B illustrates the results from the 3% H2O2 pretreated coal in chemical solubilization and conversion.

FIG. 19B displays the results from the 3% H2O2, pretreated coal experiments. The spectrum for the untreated coal in tartrate solution does not exhibit any strong absorbance peaks in the spectra (red curve). However, the pretreated coal in tartrate solution shows a peak around 225 nm and an absorbance of about 0.634 A (blue curve). This shows the pretreatment has a very strong effect on the chemical solubilization of the coal using tartrate solution. The spectra in FIG. 19B also illustrate a shift in peaks from 225 nm to about 243 nm, which occurs when the tartrate product was added to the MnP solution (green curve—0 min). This absorbance (green curve—0 min) continues to decrease over time to about 0.286 A (pink curve—15 min, turquoise curve—30 min, yellow curve—45 min, gray curve—1 hr).

Figure 19C:
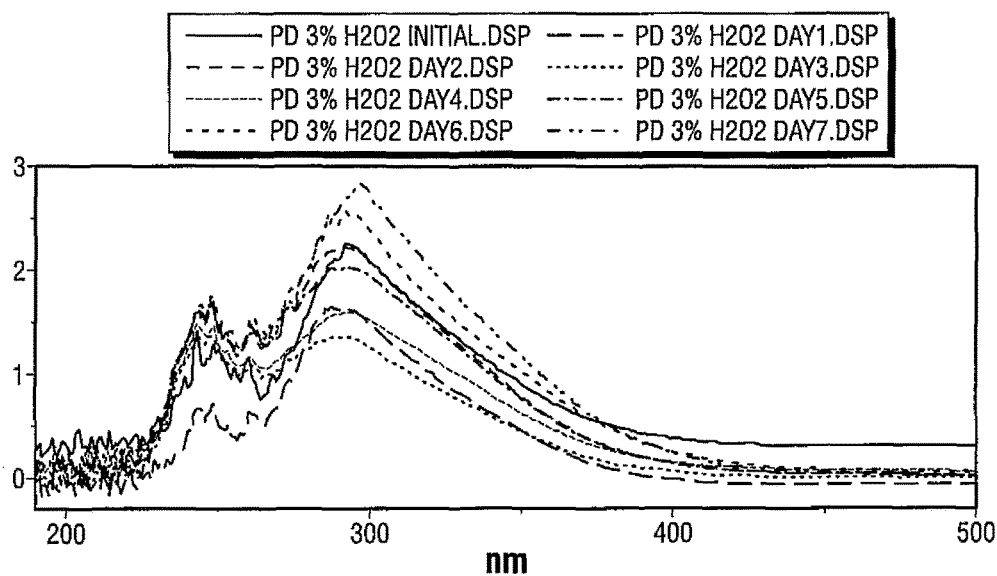
FIG. 19C illustrates the results from the 3% H2O2 pretreated coal in PD growth medium containing *P. chrysosporium*.

FIG. 19C illustrates the results from the 3% H2O2, pretreated coal experiment in PD growth medium containing *P. chrysosporium*. The spectrum for the pretreated coal in these growth conditions initially displays a peak around 245 nm with an absorbance of about 1.30 A and a peak around 290 nm with an absorbance of about 2.10 A (red curve). These peaks do not shift in wavelength (nm) over time, but the absorbance (A) each day does tend to change slightly. On Day 1, the absorbance decreases to about 0.52 A at 245 nm and 1.60 A at 290 nm (blue curve), but increases to about 1.45 A at 245 nm and 2.20 A at 290 nm on Day 2 (green curve). After Day 2, the absorbance decreases again on Day 3 to 1.28 A at 245 nm and 1.35 A at 290 nm (pink curve). Absorbance then continues to increase for the remaining days. Day 4: 1.36 A at 245 nm and 1.58 A at 290 nm (turquoise curve); Day 5: 1.51 A at 245 nm and 2.02 A at 290 nm (yellow curve); Day 6: 1.56 A at 245 nm and 2.48 nm at 290 nm (gray curve); Day 7: 1.52 A at 245 nm and 2.63 A at 290 nm (black curve).

Figure 19D:
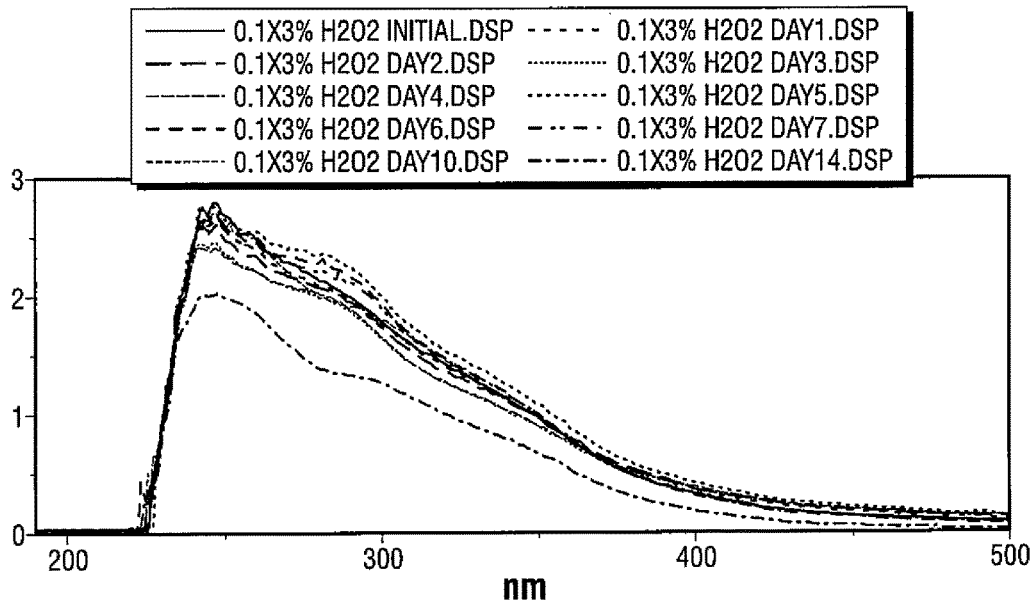
FIG. 19D illustrates the results from the 3% H2O2 pretreated coal in 0.1×SD growth medium containing *P. chrysosporium*.

FIG. 19D shows the results from the 3% H2O2, pretreated coal experiment in SD growth medium, with one tenth the amount of peptone (0.1×), containing *P. chrysosporium*. The spectrum for the pretreated coal in these growth conditions initially displays a peak around 245 nm and an absorbance of 2.73 A (red curve). This peak at 245 nm does not shift in wavelength and does not increase or decrease significantly in absorbance from Day 1 through Day 10. Day 1: 2.52 A (blue curve); Day 2: 2.57 A (green curve); Day 3: 2.42 A (pink curve), Day 4: 2.39 A (turquoise curve); Day 5: 2.71 A (yellow curve); Day 6: 2.66 A (gray curve); Day 7: 2.52 A (black curve); Day 10: 2.60 A (orange curve). The absorbance at 245 nm then decreases on Day 14 to 2.02 A (beige curve).

15% H2O2 Pretreated Coal

Figure 19E:
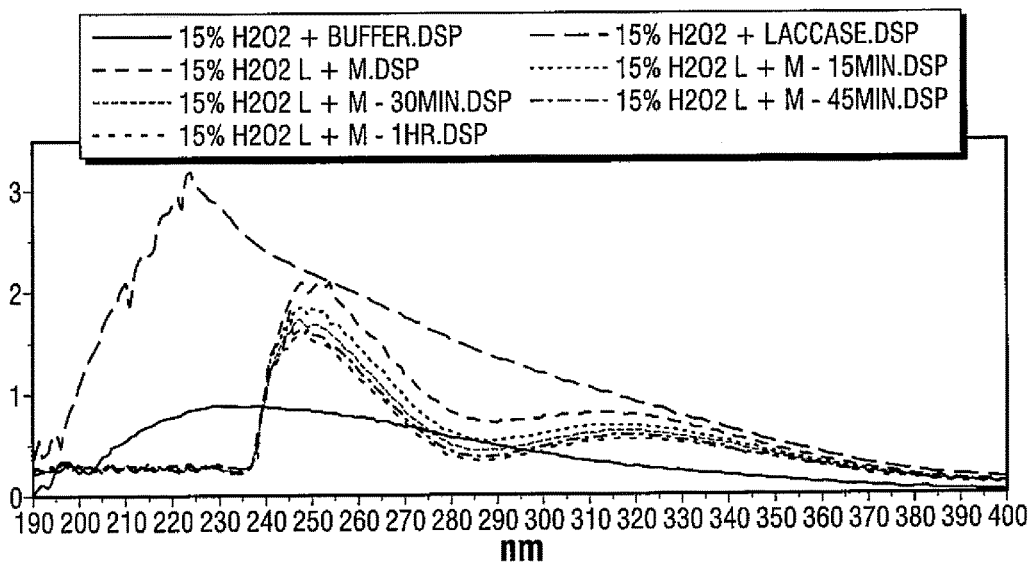
FIG. 19E illustrates the results from the 15% H2O2 pretreated coal in enzymatic solubilization and conversion.

FIG. 19E shows the results from the 15% H2O2, pretreated coal experiments. The spectrum for the pretreated coal in laccase buffer shows a peak around 230 nm and an absorbance of only about 0.877 A (red curve). This spectrum can be compared to the spectrum of the pretreated coal in laccase solution, which shows a peak around 224 nm and an absorbance of about 3.20 A (blue curve). By comparing these spectra, it can be seen that the pretreatment does have an impact on the solubilization of the coal, but that the laccase is needed for further solubilization. The spectra in FIG. 19E also illustrate a shift in peaks from 224 nm to about 249 nm and a decrease in absorbance from 3.20 A to 1.99 A, which occurs when the laccase product was initially added to the MnP solution (green curve—0 min). This absorbance (green curve—0 min) continues to decrease over time to about 1.63 A (pink curve—15 min, turquoise curve—30 min, yellow curve—45 min, gray curve—1 hr).

Figure 19F:
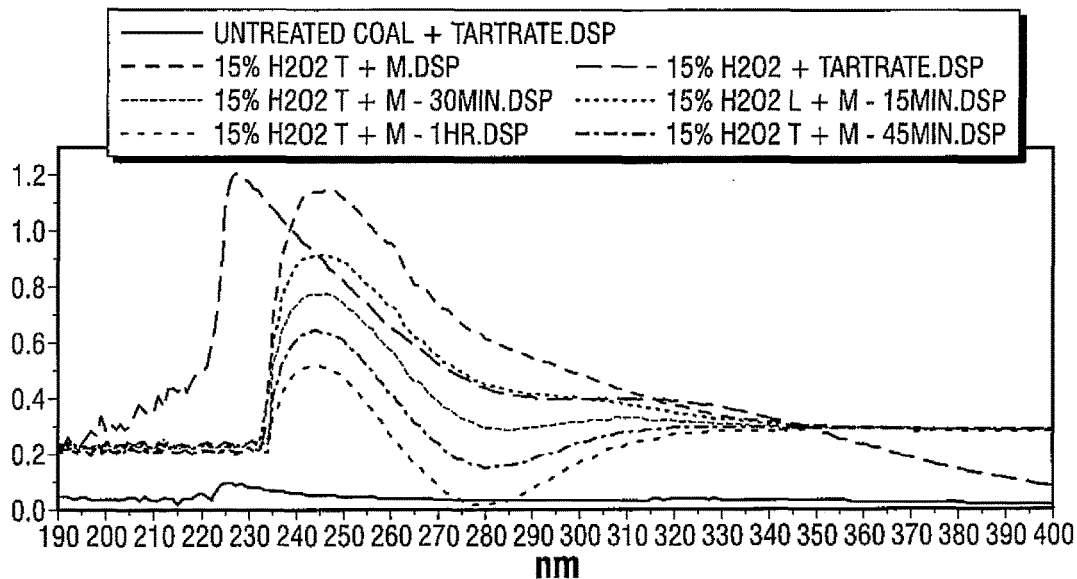
FIG. 19F illustrates the results from the 15% H2O2 pretreated coal in chemical solubilization and conversion.

FIG. 19F shows the results from 15% H2O2, pretreated coal experiments. The spectrum for the untreated coal in tartrate solution does not exhibit any strong absorbance peaks in the spectra (red curve). However, the pretreated coal in tartrate solution shows a peak around 227 nm and an absorbance of about 1.21 A (blue curve). This indicates that the pretreatment has a very strong impact on the chemical solubilization of the coal in tartrate solution. The spectra in FIG. 19F also illustrate a shift in peaks from 227 nm to about 245 nm and a slight drop in absorbance from 1.21 A to 1.14

A, which occurs when the tartrate product was initially added to the MnP solution (green curve—0 min). This absorbance (green curve—0 min) continues to decrease over time to about 0.52 A (pink curve—15 min, turquoise curve—30 min, yellow curve—45 min, gray curve—1 hr).

Figure 19G:
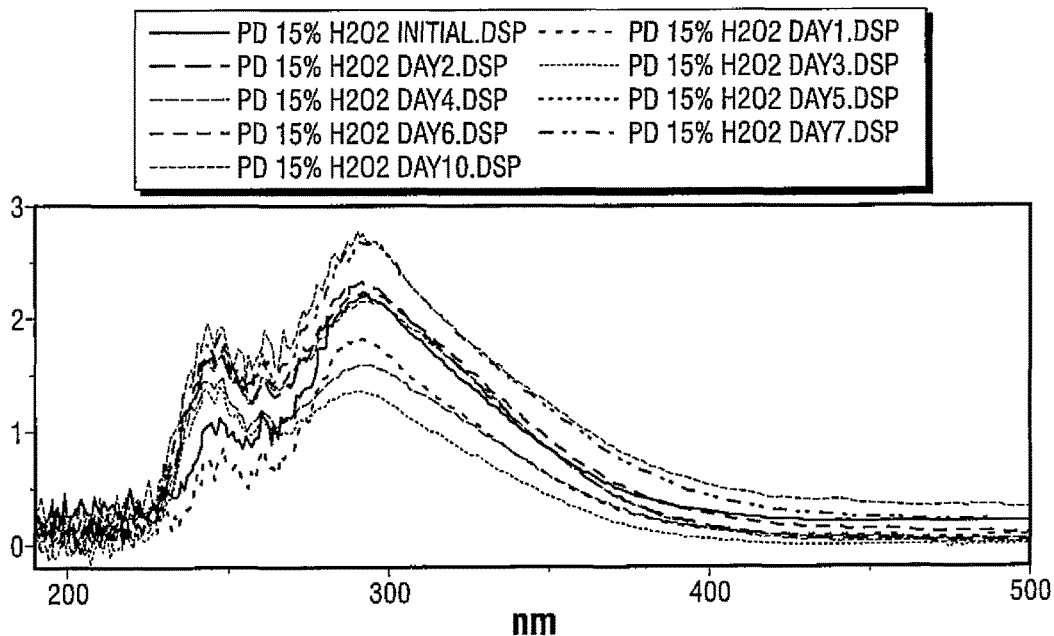
FIG. 19G illustrates the results from the 15% H2O2 pretreated coal in PD growth medium containing *P. chrysosporium*.

FIG. 19G shows the results from the 15% H2O2, pretreated coal experiment in PD growth medium containing *P. chrysosporium*. The spectrum (red curve) for the pretreated coal in these conditions initially shows two peaks: one peak at a wavelength of 245 nm with absorbance of 1.00 A and one peak at a wavelength of 290 nm with absorbance of 2.20 A. The peaks in FIG. 19G do not appear to shift in wavelength but do show changes in the absorbance from day to day. After the first day, the peak absorbance decreases from the initial peak to about 0.69 A at 245 nm and 1.80 A at 290 nm (blue curve). This absorbance then increases on Day 2 to 1.56 A at 245 nm and 2.30 A at 290 nm (green curve) and decreases on Day 3 to 1.31 A at 245 nm and 1.35 A at 290 nm (pink curve). After Day 3, the curves then increase in absorbance for the remaining days. Day 4: 1.38 A at 245 nm and 1.58 A at 290 nm (turquoise curve); Day 5: 1.53 A at 245 nm and 2.13 A at 290 nm (yellow curve); Day 6: 1.62 A at 245 nm and 2.22 A at 290 nm (gray curve); Day 7: 1.74 A at 245 nm and 2.69 A at 290 nm (black curve); Day 10:1.75 A at 245 nm and 2.76 A at 290 nm (orange curve).

Figure 19H:
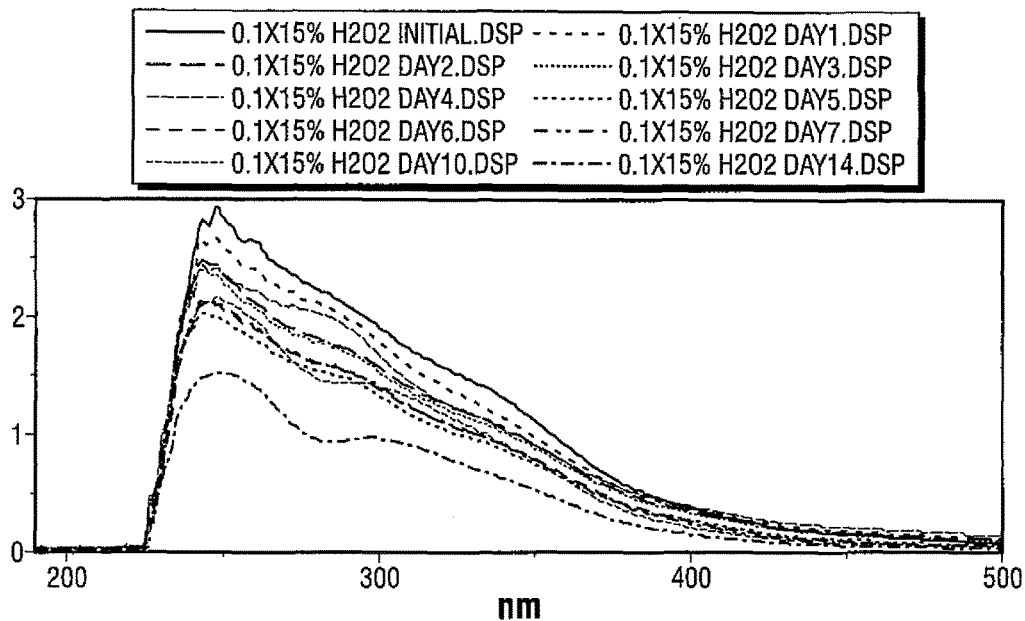
FIG. 19H illustrates the results from the 15% H2O2 pretreated coal in 0.1×SD growth medium containing *P. chrysosporium*.

FIG. 19H shows the results from the 15% H2O2, pretreated coal experiment in SD growth medium, with one tenth the amount of peptone (0.1×), containing *P. chrysosporium*. The spectrum for the pretreated coal in these growth conditions initially displays a peak around 245 nm and an absorbance of 2.78 A (red curve). This peak at 245 nm does not shift in wavelength but decreases slightly in absorbance from Day 1 through Day 14. Day 1: 2.64 A (blue curve); Day 2: 2.45 A (green curve); Day 3: 2.38 A (pink curve), Day 4: 2.39 A (turquoise curve); Day 5: 2.02 A (yellow curve); Day 6: 2.09 A (gray curve); Day 7: 2.12 A (black curve); Day 10: 2.13 A (orange curve); Day 14: 1.50 A (beige curve).

30% H2O2 Pretreated Coal

Figure 19I:
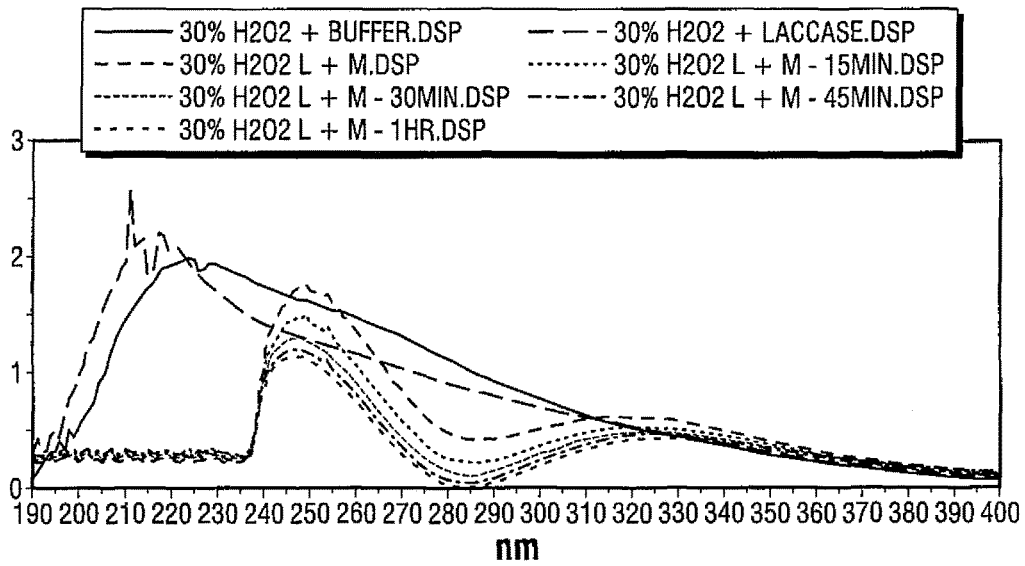
FIG. 19I illustrates the results from the 30% H2O2 pretreated coal in enzymatic solubilization and conversion.

FIG. 19I shows the results from the 30% H2O2, pretreated coal experiments. The spectrum for the pretreated coal in laccase buffer shows a peak around 224 nm and an absorbance of about 1.99 A (red curve). This spectrum can be compared to the spectrum of the pretreated coal in laccase solution, which shows a peak around 211 nm and an absorbance of about 2.58 A (blue curve). The comparison of these spectra illustrates that the 30% pretreatment by itself is almost as effective as the laccase in solubilizing the coal. The spectra in FIG. 19I also illustrate a shift in peaks from 211 nm to about 249 nm and a decrease in absorbance from 2.58 A to 1.77 A, which occurs when the laccase product was initially added to the MnP solution (green curve). This absorbance (green curve) also continues to decrease over time to about 1.13 A (pink curve—15 min, turquoise curve—30 min, yellow curve—45 min, gray curve—1 hr).

FIG. 19J shows the results from the 30% H2O2, pretreated coal experiments. The spectrum for the untreated coal in tartrate solution does not exhibit any strong absorbance peaks in the spectra (red curve). However, the pretreated coal in tartrate solution shows a peak around 228 nm and an absorbance of about 1.52 A (blue curve). The difference in these peaks shows the pretreatment is necessary to chemically solubilize the coal in tartrate solution. The spectra in FIG. 19J also illustrates a shift in peaks from 228 nm to about 245 nm and a drop in absorbance from 1.52 A to 1.18 A, which occurs when the tartrate product was added to the MnP solution (green curve—0 min). This absorbance (green curve—0 min) continues to decrease over time to about 0.87 A (pink curve—15 min, turquoise curve—30 min, yellow curve—45 min, gray curve—1 hr).

FIG. 19K shows the results from the 30% H2O2, pretreated coal experiment in PD growth medium containing *P. chrysosporium*. The spectrum for this particular pretreated coal initially shows a peak around 245 nm with an absorbance of about 0.86 A and a peak around 295 nm with an absorbance of 1.89 A (red curve). After the first day, the absorbance drops to about 0.59 A at 245 nm, but remains at about 0.86 A at 295 nm (blue curve). From Day 2 to Day 5, the absorbance at 245 nm does not change significantly, while the peak at 295 nm changes slightly each day. Day 2: 1.54 A at 245 nm and 2.56 A at 295 nm (green curve); Day 3: 1.38 A at 245 nm and 2.22 A at 295 nm (pink curve); Day 4: 1.57 A at 245 nm and 2.26 A at 295 nm (turquoise curve); Day 5: 1.76 A at 245 nm and 2.83 A at 295 nm (yellow curve). On Day 6, the absorbance increases at both peaks to about 2.29 A at 245 nm and 3.46 A at 295 nm (gray curve).

Figure 19L:
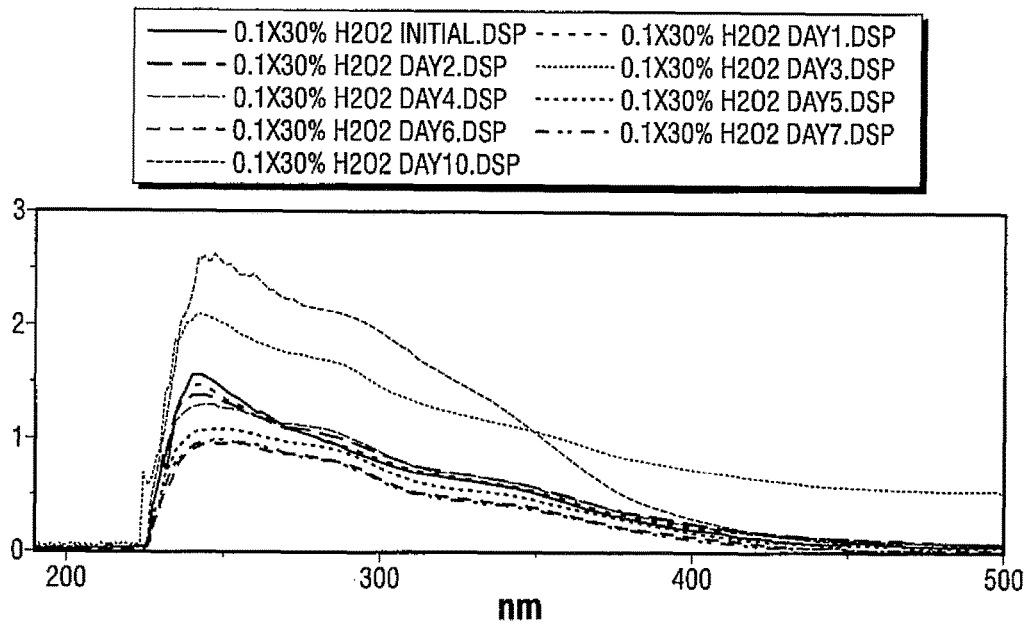
FIG. 19L illustrates the results from the 30% H2O2 pretreated coal in 0.1×SD growth medium containing *P. chrysosporium*.

FIG. 19L shows the results from the 30% H2O2, pretreated coal experiment in SD growth medium, with one tenth the amount of peptone (0.1×), containing *P. chrysosporium*. The spectrum for the pretreated coal in these growth conditions initially displays a peak around 243 nm and an absorbance of 1.56 A (red curve). This peak at 245 nm does not shift in wavelength but decreases in absorbance over Day 1 through Day 7, with the exception of Days 3 and 10 which increase in absorbance. Day 1: 1.47 A (blue curve); Day 2: 1.39 A (green curve); Day 3: 2.09 A (pink curve), Day 4: 1.30 A (turquoise curve); Day 5: 1.07 A (yellow curve); Day 6: 0.93 A (gray curve); Day 7: 0.93 A (black curve). On Day 10, the absorbance at 245 nm increases to 2.58 A (orange curve).

Heated Coal Pretreatment

Figure 19M:
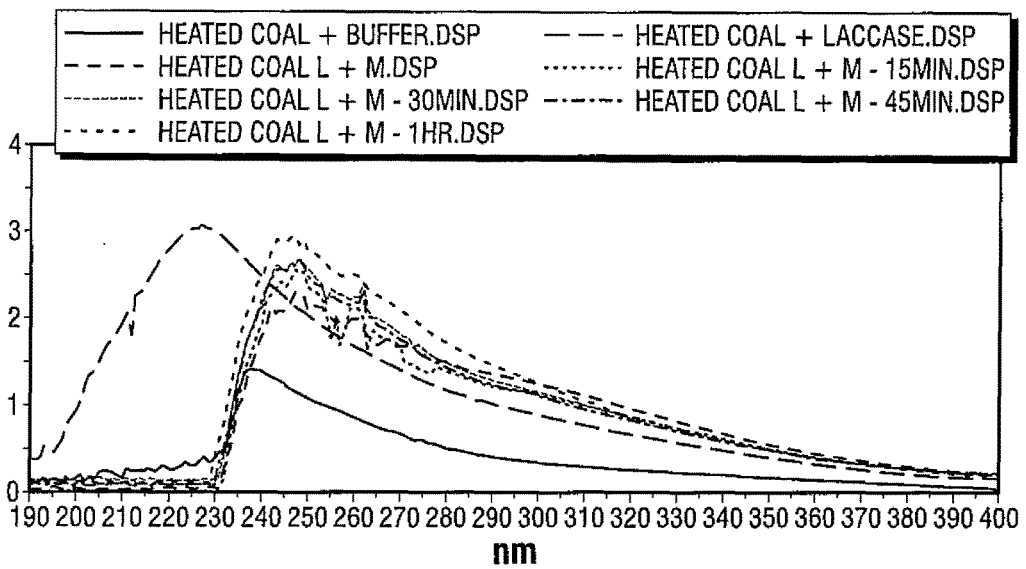
FIG. 19M illustrates the results from the heated, 30% H2O2 pretreated coal in enzymatic solubilization and conversion.

FIG. 19M shows the results from the heated, 30% H2O2, pretreated coal experiments. The spectrum for the pretreated coal in laccase buffer shows a peak around 237 nm and an absorbance of only about 1.41 A (red curve). This spectrum can be compared to the spectrum of the pretreated coal in laccase solution, which shows a peak around 227 nm and an absorbance of about 3.09 A (blue curve). The comparison of these spectra shows that the pretreatment does have some effect on the coal solubilization, but that the laccase further oxidizes the coal for solubilization. The spectra in FIG. 19M also illustrate a shift in peaks from 227 nm to about 247 nm and a decrease in absorbance from 3.09 A to 2.31 A, which occurs when the laccase product was initially added to the MnP solution (green curve—0 min). This curve also continues to change over time (pink curve—15 min, turquoise curve—30 min, yellow curve—45 min, gray curve—1 hr).

Figure 20A:
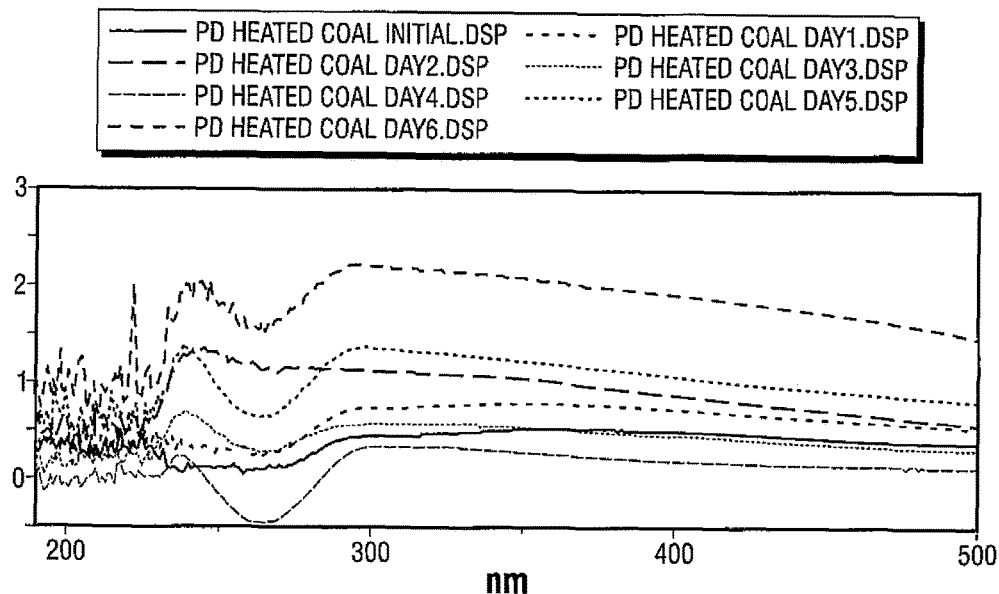
FIG. 20A illustrates the results from the heated coal in PD growth medium containing *P. chrysosporium*.

FIG. 20A shows the results from the heated coal experiment. The spectrum for this pretreatment in PD growth medium with *P. chrysosporium* does not initially display a strong peak on Day 0 (red curve) or Day 1 (blue curve). A peak then starts to form on Day 2 around 240 nm with an absorbance of 1.39 A (green curve). This peak at 240 nm then decreases in absorbance on Day 3 to 0.68 A (pink curve) and Day 4 to 0.23 A (turquoise curve). Finally, the peak increases in absorbance at 240 nm over the last 2 days. Day 5: 1.39 A at 245 nm (yellow curve) and Day 6: 1.93 A at 240 nm (gray curve).

Figure 20B:
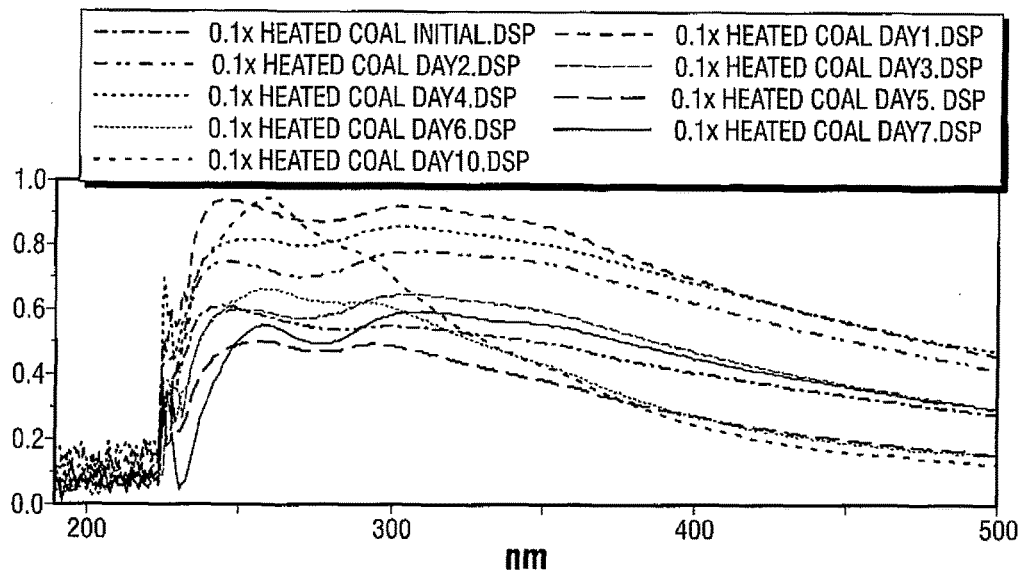
FIG. 20B illustrates the results from the heated coal in 0.1×SD growth medium containing *P. chrysosporium*.

FIG. 20B shows the results from the heated coal experiment in SD growth medium, with one tenth the amount of peptone (0.1×), containing *P. chrysosporium*. The spectrum for the pretreated coal in these conditions initially shows a peak at about 240 nm and an absorbance of 0.61 A (red curve). This peak at 240 nm then increases in absorbance to about 0.78 A on Day 1 (blue curve). From Day 2 through Day 5, the absorbance at this wavelength continues to change. Day 2: 0.73 A (green curve); Day 3: 0.56 A (pink curve); Day 4: 0.78 A (turquoise curve); Day 5: 0.44 A (yellow curve). On Day 6 the wavelength appears to shift to about 260 nm and remains at this wavelength on Day 7 and Day 10. Day 6: 0.66 A (gray curve); Day 7: 0.55 A (black curve) and Day 10: 0.95 A (orange curve).

Mine Water Pretreated Coal

Figure 21A:
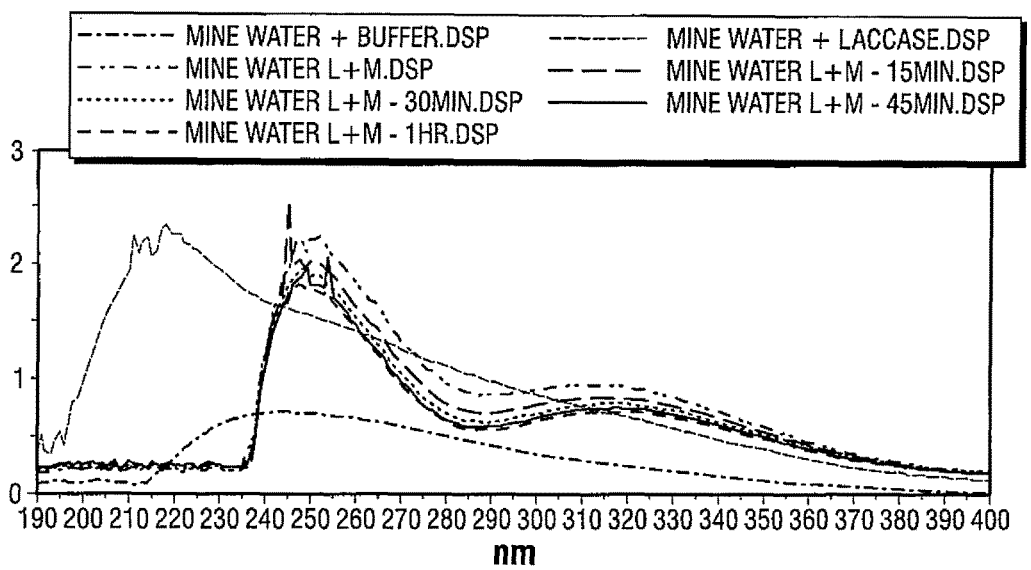
FIG. 21A illustrates the results from the mine water pretreated coal in enzymatic solubilization and conversion.

FIG. 21A illustrates the results from the mine water, pretreated coal experiments. The spectrum for the pretreated coal in laccase buffer shows a peak around 245 nm and an absorbance of about 0.71 A (red curve). This spectrum can be compared to the spectrum of the pretreated coal in laccase solution, which shows a peak around 217 nm and an absorbance of about 2.34 A (blue curve). The comparison of these spectra shows that this pretreatment does help to initially oxidize and decompose the coal, but that the laccase is necessary for further decomposition. The spectra in FIG. 21A also illustrate a shift in peaks from 217 nm to about 249 nm and a slight decrease in absorbance from 2.58 A to 2.25 A, which occurs when the laccase product was initially added to the MnP solution (green curve—0 min). This absorbance (green curve—0 min) continues to decrease over time to about 1.83 A (pink curve—15 min, turquoise curve—30 min, yellow curve—45 min, gray curve—1 hr).

Figure 21B:
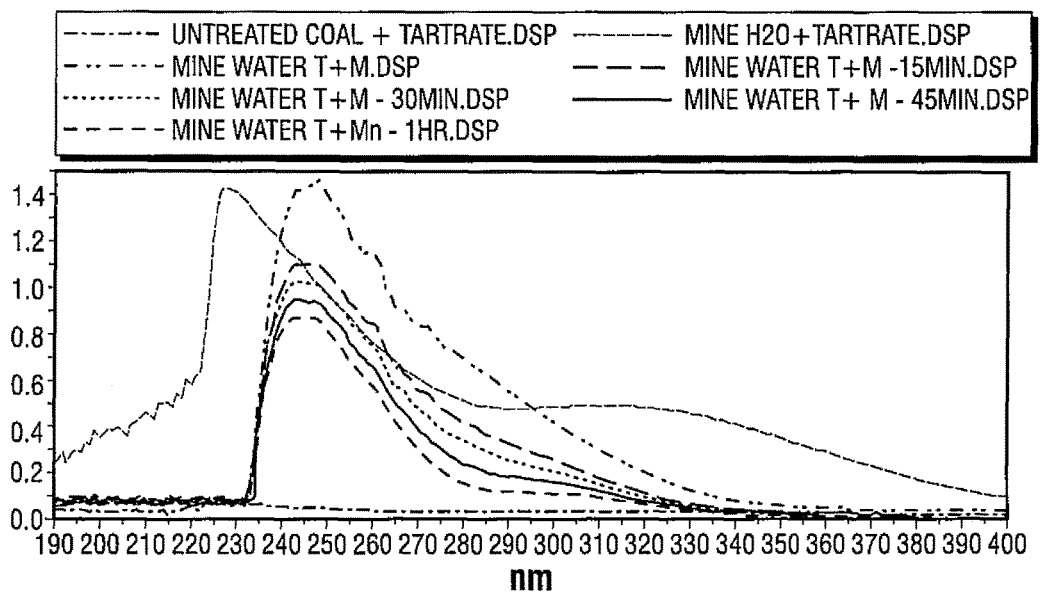
FIG. 21B illustrates the results from the mine water pretreated coal in chemical solubilization and conversion.

FIG. 21B shows the results from the mine water, pretreated coal experiments. The spectrum for the untreated coal in tartrate solution does not exhibit any strong absorbance peaks in the spectra (red curve). However, the pretreated coal in tartrate solution shows a peak around 228 nm and an absorbance of about 1.43 A (blue curve). The comparison of these two curves shows that the pretreatment is necessary to chemically solubilize the coal in tartrate solution. The spectra in FIG. 21B also illustrate a shift in peaks from 228 nm to about 245 nm, which occurs when the tartrate product was added to the MnP solution (green curve—0 min). This absorbance (green curve—0 min) continues to decrease over time to about 0.87 A (pink curve—15 min, turquoise curve—30 min, yellow curve—45 min, gray curve—1 hr).

Figure 21C:
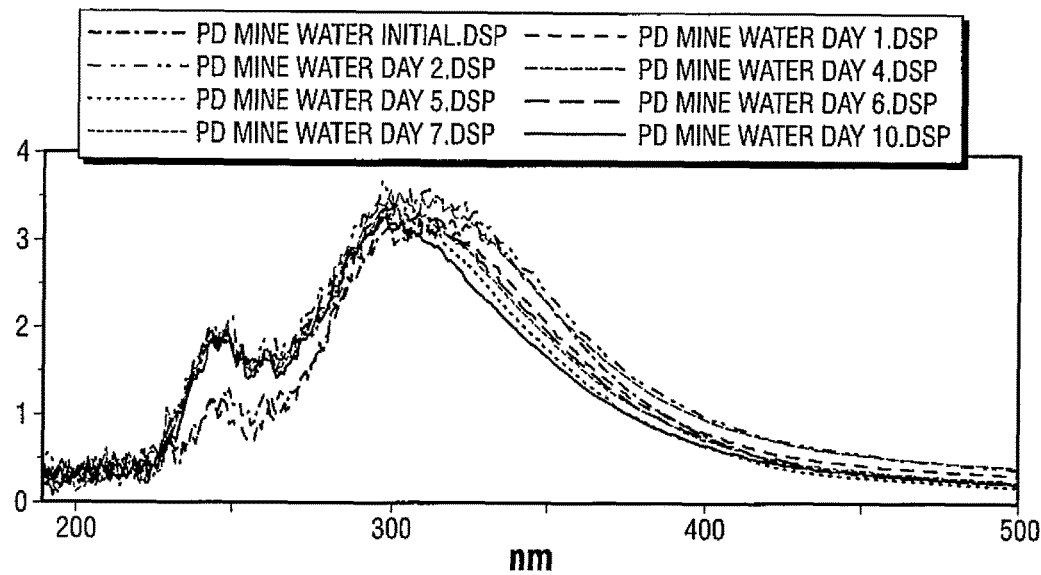
FIG. 21C illustrates the results from the mine water pretreated coal in PD growth medium containing *P. chrysosporium*.

FIG. 21C illustrates the results from the mine water, pretreated coal experiment in PD growth medium containing *P. chrysosporium*. The spectrum for this pretreated coal shows 2 peaks: one peak around 245 nm and one peak around 305 nm. The peak at 245 nm initially has an absorbance of 1.17 A (red curve) and remains at 1.17 A after Day 1 (blue curve). The peak at 245 nm then increases in absorbance on Day 2 to about 2.00 A (green curve) and only changes slightly in absorbance over the remaining days. Day 4: 1.84 A (pink curve); Day 5: 1.89 A (turquoise curve); Day 6: 1.87 A (yellow curve); Day 7: 1.78 A (gray curve); Day 10:1.82 A (black curve). The peak at 305 nm has an initial absorbance of 2.97 A (red curve) and also changes very slightly over the time period. Day 1: 3.06 A (blue curve); Day 2: 3.51 A (green curve); Day 4: 3.49 A (pink curve); Day 5: 3.12 A (turquoise curve); Day 6: 3.31 A (yellow curve); Day 7: 3.24 A (gray curve); Day 10: 3.06 A (black curve).

Figure 21D:
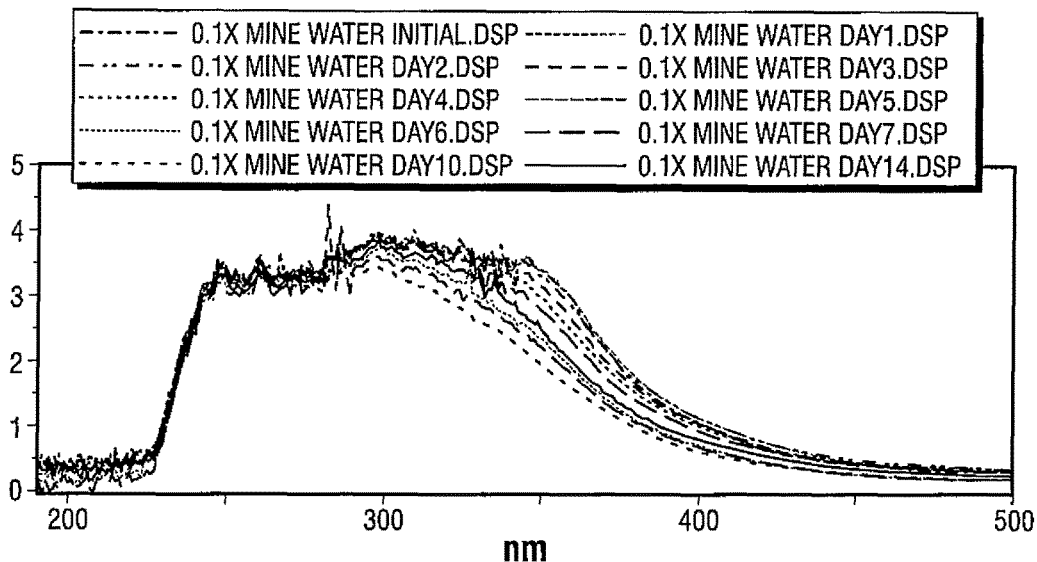
FIG. 21D illustrates the results from the mine water pretreated coal in 0.1×SD growth medium containing *P. chrysosporium*.

FIG. 21D shows the results from the mine water, pretreated coal experiment in SD growth medium, with one tenth the amount of peptone (0.1x), containing *P. chrysosporium*. The spectrum for the pretreated coal in these conditions initially shows a broad peak around 297 nm with an absorbance of about 3.94 A (red curve). The spectra for Day 1 through Day 5 remains relatively unchanged at 297 nm. Day 1: 3.95 A (blue curve); Day 2: 3.96 A (green curve); Day 3: 3.89 A (pink curve); Day 4: 3.97 A (turquoise curve); Day 5: 3.82 A (yellow curve). On Day 6 the absorbance begins to decrease slightly at 297 nm and continues to decrease slightly on Day 7 and Day 10. Day 6: 3.70 A (gray curve); Day 7: 3.60 A (black curve); Day 10: 3.45 A (orange curve). On Day 14, the absorbance increases to 3.76 A (beige curve).

HNO3 (pH 1) Pretreated Coal

Figure 22A:
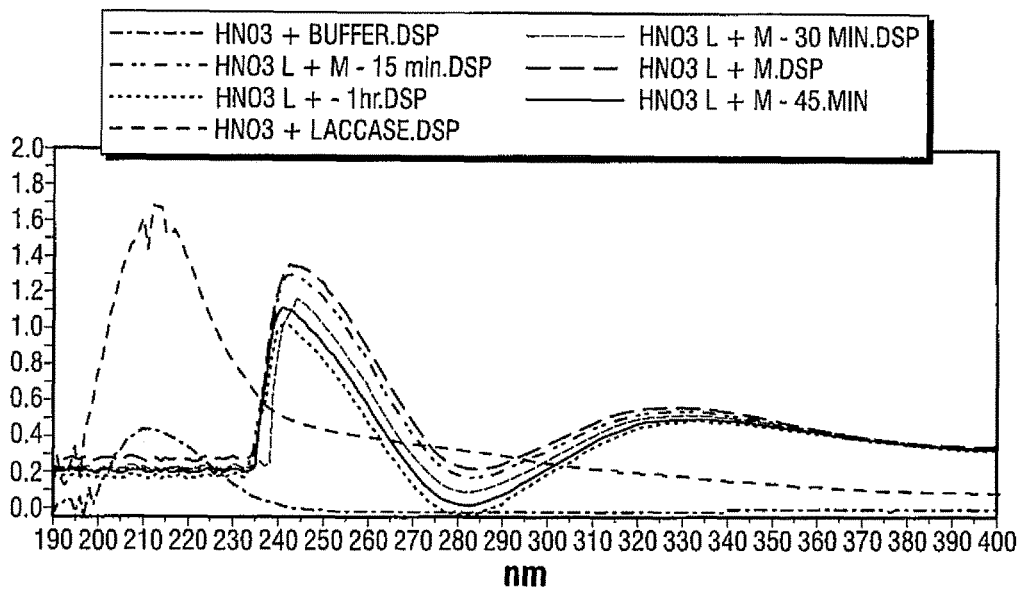
FIG. 22A illustrates the results from the HNO3 (pH 1) pretreated coal in enzymatic solubilization and conversion.

FIG. 22A shows the results from the HNO3 (pH 1), pretreated coal experiments. The spectrum for the pretreated coal in laccase buffer shows a peak around 210 nm and an absorbance of about only 0.47 A (red curve), and can be compared to the spectrum for the pretreated coal in laccase solution, which shows a peak around 213 nm and an absorbance of about 1.68 A (blue curve). The comparison of these curves indicates that the pretreatment does have an effect on coal solubilization, but that the laccase solution works to further oxidize and decompose the coal. The spectra in FIG. 22A also illustrate a shift in peaks from 213 nm to about 244 nm and a decrease in absorbance from 1.68 A to 1.35 A, which occurs when the laccase product was initially added to the MnP solution (green curve—0 min). This absorbance (green curve—0 min) continues to decrease over time to about 0.99 A (pink curve—15 min, turquoise curve—30 min, yellow curve—45 min, gray curve—1 hr).

Figure 22B:
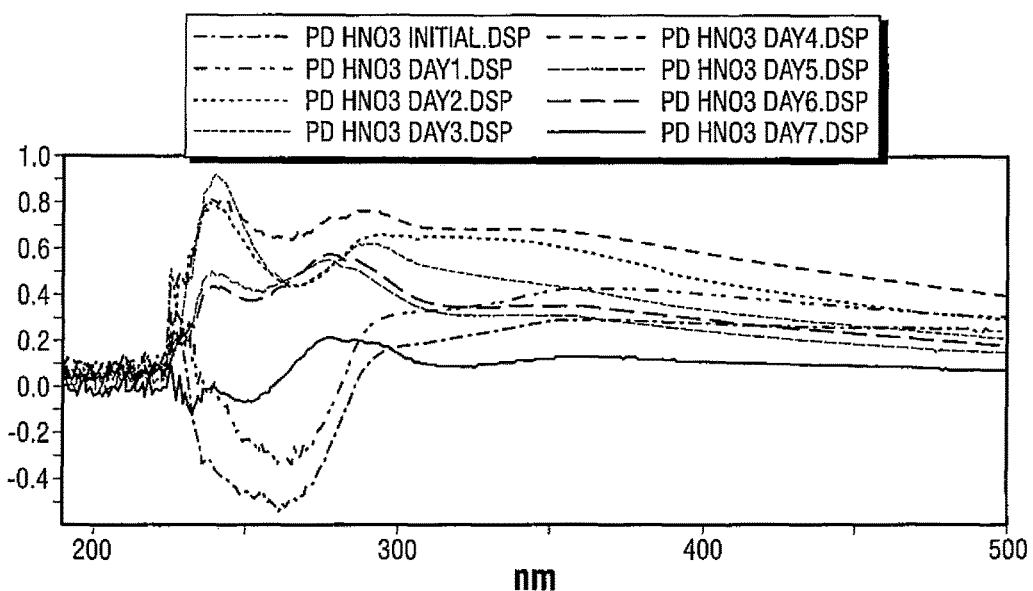
FIG. 22B illustrates the results from the HNO3 (pH 1) pretreated coal in PD growth medium containing *P. chrysosporium*.

FIG. 22B shows the results from the HNO3 (pH 1), pretreated coal experiment in PD growth medium containing *P. chrysosporium*. The spectrum for this experiment initially shows a peak around 260 nm with a relative absorbance of −0.52 A (red curve). This absorbance at 260 nm increases in absorbance to −0.32 A on Day 1 (blue curve). On Day 2 the peak shifts and begins to form at 240 nm with an absorbance of 0.794 A (green curve). This peak at 240 nm slightly increases on Day 3 to 0.93 A (pink curve), but then continues to decrease in absorbance from Day 4 to Day 7. Day 4: 0.80 A (turquoise curve); Day 5: 0.49 A (yellow curve); Day 6: 0.44 A (gray curve); Day 7: 0.003 A (black curve).

Figure 22C:
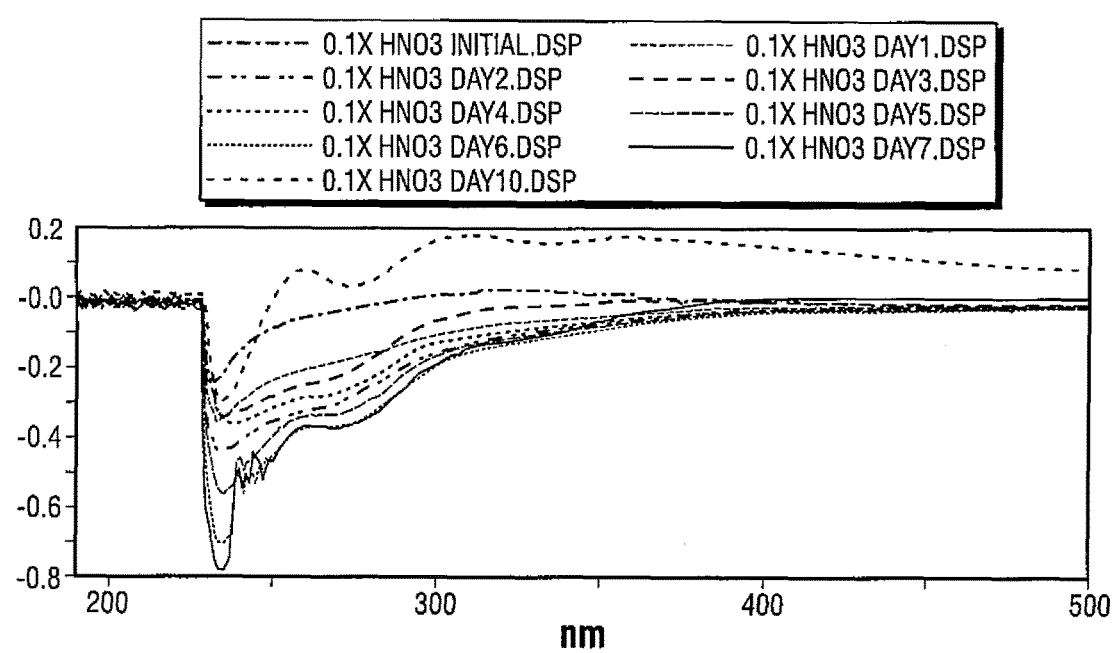
FIG. 22C illustrates the results from the HNO3 (pH 1) pretreated coal in 0.1×SD growth medium containing *P. chrysosporium*.

FIG. 22C shows the results from the HNO3 (pH 1), pretreated coal experiment in SD growth medium, with one tenth the amount of peptone (0.1x), containing *P. chrysosporium*. The spectrum for the pretreated coal in these conditions initially shows an absorbance of −0.23 A around 235 nm (red curve). The absorbance at this wavelength then continues to decrease on Day 1 through Day 7. Day 1: −0.35 A (blue curve); Day 2: −0.44 A (green curve); Day 3: −0.34 A (pink curve); Day 4: −0.33 A (turquoise curve); Day 5: −0.55 A (yellow curve); Day 6: −0.70 A (gray curve); Day 7: −0.78 A (black curve). Finally on Day 10, the absorbance at 235 nm increases to about −0.30 A (orange curve).

Figure 23:
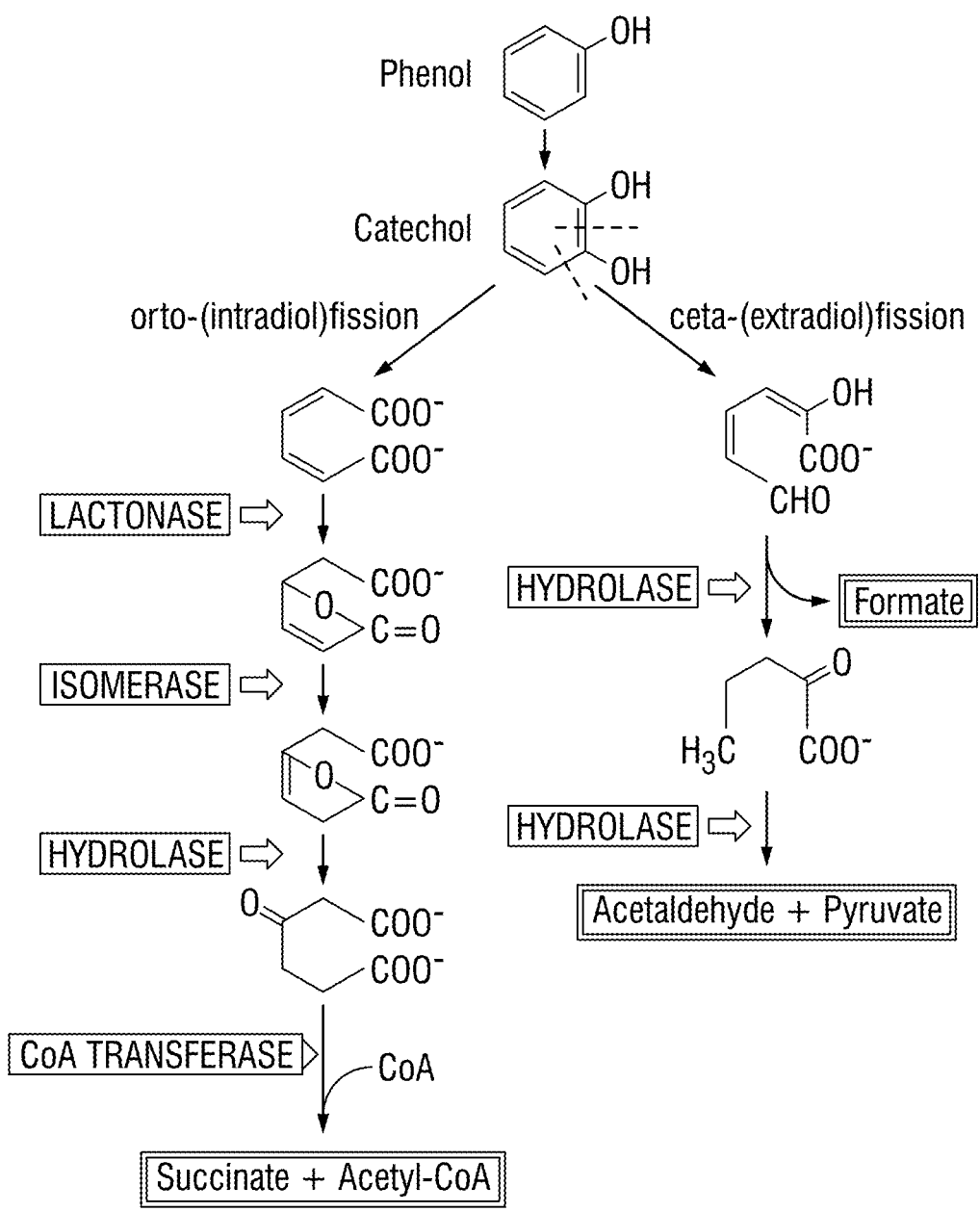
FIG. 23 (prior art) is a simplified diagram showing microbial degradation of phenol.

The work for this example focused on conversion of bituminous coal to liquid fuels. This process involves the same steps taken by natural microorganisms to break down the molecular structures found in coal into useable forms that can enter their metabolic pathways for the release of carbon and energy. One example of such a pathway is the digestion of phenol, given in FIG. 23.

Phenols represent a important class of functional groups since 40-75% of the carbon in bituminous coal is aromatic, and phenols and phenolic moieties represent the preferred entry point for microbial aromatic ring cleavage.

Figure 24:
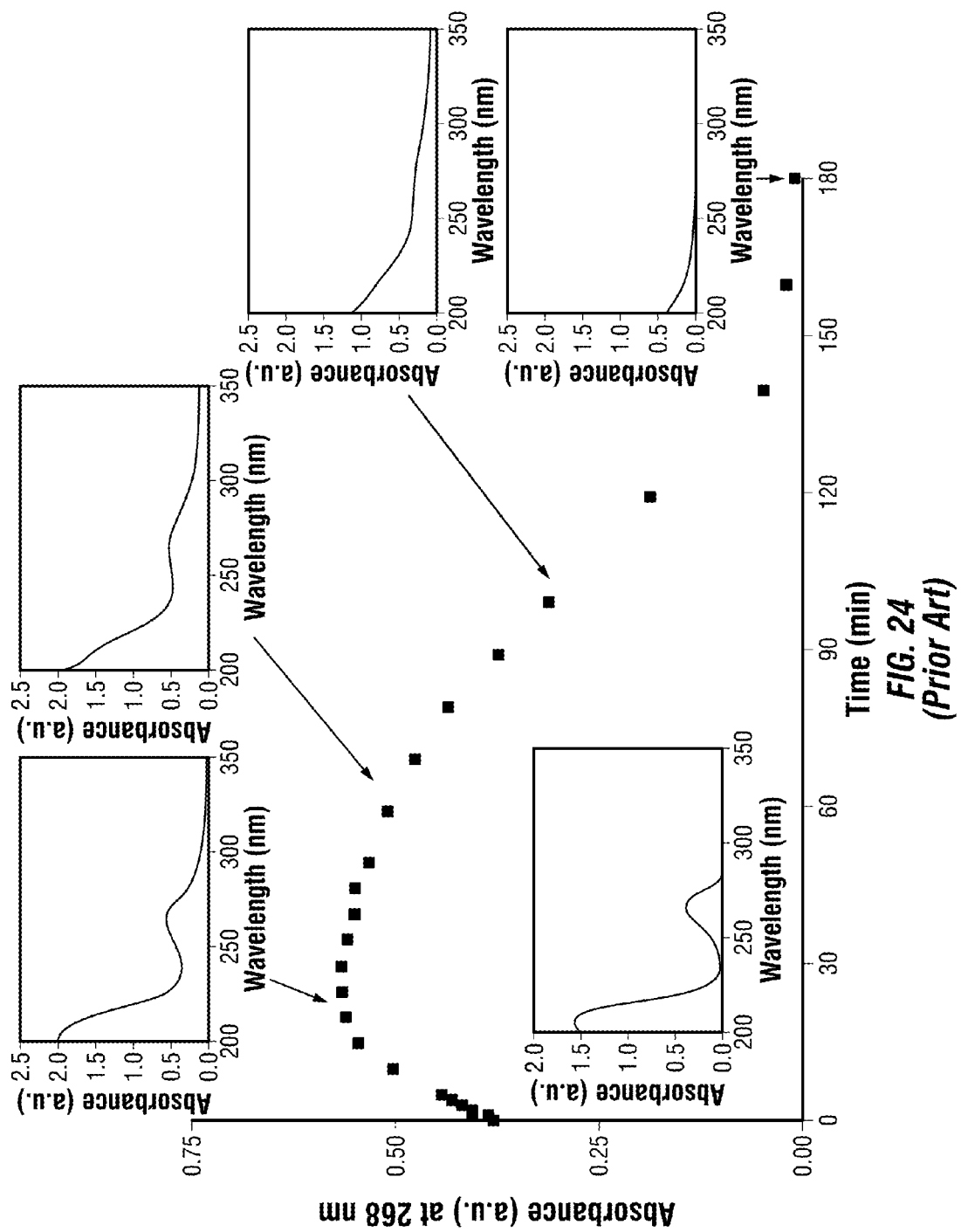
FIG. 24 (prior art) illustrates UV spectra for phenol degradation.

Opening aromatic ring structures is also a necessary first step in the conversion of coal to liquid fuels in the CFS process. For reference, a time series of UV spectra for phenol degradation is given in FIG. 24. While these results were not obtained from a biological system, they do provide a qualitative measure of the transitions in UV spectra that can be expected from the reaction pathway shown above.

As the graph shows, absorbance at the front end of the UV spectra increases during the initial stages of degradation corresponding to the formation of aromatic intermediates. As more intermediates are formed, the concentration of phenol decreases, shown by the decrease in absorbance for phenol at 268 nm. Both peaks then begin to decrease as the phenol is consumed and the aromatic intermediates undergo ring cleavage. Eventually absorbance approaches zero as the cleaved aromatic intermediates are converted to organic acids.

The spectra presented in this example show that the methods used in this example produce the same type of degradation as shown in the UV spectra for phenol degradation. It is also clear that the extent to which coal undergoes conversion varies significantly with the way the coal is pretreated.

As previously described, three different approaches were taken to degrade bituminous coal: (1) laccase and MnP, (2) tartrate and MnP, and (3) live P. chrysosporium using two different growth media. The results from the laccase and MnP experiments and live P. chrysosporium experiments show the best results and are compared.

These spectra are shown in FIGS. 19A through 22C. As seen in FIGS. 19A through 22C, the spectra for these approaches using various pretreatments of coal display peaks in the 240 nm to 300 nm region. These peaks correspond to the smaller aromatic ring intermediates and organic acids formed from the degradation of bituminous coal. From these spectra, it is apparent that both of the methods do work to degrade coal.

The first enzymatic solubilization and conversion experiments were conducted using laccase and MnP, shown in FIGS. 19A, 19E, 19I, 19M, 21A, and 22A. The spectra show peaks around 245 nm-250 nm. The peaks in these spectra start to decrease in absorbance over a period of 1 hour, corresponding to the consumption of aromatic intermediates as they undergo ring cleavage.

Live P. chrysosporium was used as another method to degrade bituminous coal. It was grown in two different growth media to provide sufficient growth conditions for the organism to excrete extracellular enzymes to degrade coal. The spectra from the potato dextrose (PD) growth medium containing P. chrysosporium display peaks in the 240 nm to 300 nm region, shown in FIGS. 19C, 19G, 19K, 20A, 21C, and 22B. The peak absorbance is shown to decrease over a period of 7 to 10 days in these experiments.

P. chrysosporium was also grown in a Sabouraud Dextrose (SD) growth medium. The spectra corresponding to these experiments are shown in FIGS. 19D, 19H, 19L, 20B, 21D, and 22C. Most of the peaks in the spectra are seen around 235 nm to 245 nm. A decrease in peak absorbance can be seen over a period of 10 to 14 days.

The main parameters compared between the UV-VIS spectra for the two different enzymatic methods were the location of the peaks (nm) and the decrease in peak absorbance (A). As mentioned, the peaks from the experiments fall in the range of 240 nm to 300 nm, which correspond to aromatic intermediates formed when breaking down the coal structure. The peaks from the laccase+MnP and P. chrysosporium in the S.D. growth medium experiments show similar peaks in the 235 nm to 250 nm region. The peaks from the P. chrysosporium in the P.D. growth medium show two different peaks, in the 245 nm region and in the 290 nm region.

When comparing the decreases in peak absorbance, it can be seen that the experiments conducted with laccase and MnP experiments decrease in absorbance over the time period of 1 hour. However, in the live P. chrysosporium experiments, the decrease in peak absorbance is seen over a period of 10 to 14 days. This is a significant difference in the time it takes for the aromatic intermediates to form and ring cleavage to occur, and illustrates one of the major differences between using extracellular enzymes and using live organisms.

When comparing the spectra among the different types of pretreatment, it can be seen that the most consistent results are seen in the 3%, 15%, and 30% hydrogen peroxide pretreatments. These spectra show peaks in the 235 nm to 240 nm region for all of the pretreated coal samples. In the spectra for the heated coal, the peaks for the experiments using live P. chrysosporium are not as consistent as the peaks for the experiments using extracellular enzymes. In the mine water pretreated coal, the peaks do not decrease in absorbance over time in the experiments using live P. chrysosporium as they do in the experiments using extracellular enzymes. Finally, the spectra for the nitric acid pretreated coal show negative absorbance in the experiments using live P. chrysosporium, which is not consistent with the peaks obtained using extracellular enzymes.

In this example, it has been shown that both extracellular enzymes and live organisms can be used to decompose bituminous coal. The spectra from these experiments show peaks in 240 nm to 300 nm region, corresponding to the smaller aromatic ring intermediates and organic acids formed from the degradation coal. However, when comparing these different methods, it is apparent that the most efficient way to attack the coal structure is with enzymes. This process has a few advantages over using live organisms.

One of the main advantages of using extracellular enzymes instead of live organisms is the time necessary for decomposition. As seen in the spectra, the results from the experiments using the laccase and manganese peroxidase showed a decrease in absorbance within the first hour of experimentation. Similar decreases in absorbance are also seen in the P. chrysosporium results. However, these results were recorded over days, rather than minutes. It obviously takes a longer time for the live organism to excrete the proper extracellular enzymes to degrade coal.

In addition, as mentioned before, working with organisms is difficult because they are alive and the number of unknowns is numerous. This includes maintaining the ideal culture conditions for the organism and also controlling contaminants and fungicidal byproducts that may prevent the organism from growing or excreting extracellular enzymes to break down coal.

Other ligninolytic enzymes, such as lignin peroxidase, may also be used to degrade bituminous coal. In addition, other types of white rot fungi, such as *Trametes Versicolor*, may be grown and exposed to bituminous coal. Different culture conditions may also affect how the organisms excrete extracellular enzymes to degrade coal.

While the preferred embodiments of the invention have been shown and described, modifications thereof can be made by one skilled in the art without departing from the spirit and teachings of the invention. The embodiments described and the examples provided herein are exemplary only, and are not intended to be limiting. Many variations and modifications of the invention disclosed herein are possible and are within the scope of the invention. Accordingly, the scope of protection is not limited by the description set out above, but is only limited by the claims that follow, the scope including all equivalents of the subject matter of the claims.

I claim:

1. A method for producing a liquid hydrocarbon product comprising,
   disintegrating a hydrocarbon source;
   pretreating the disintegrated hydrocarbon source;
   solubilizing the disintegrated hydrocarbon source to form a slurry comprising a reactant molecule of the hydrocarbon source;
   admixing a biochemical liquor into the slurry, wherein the biochemical liquor comprises at least one conversion enzyme capable of facilitating photo-fragmentation of said reactant molecule of the hydrocarbon source, and wherein the at least one conversion enzyme comprises manganese peroxidase;
   inducing fragmentation of the reactant molecule to form liquid hydrocarbons via enzyme assisted photo-fragmentation;
   separating the liquid hydrocarbons from the slurry, wherein contaminants remain in the slurry; and
   enriching the liquid hydrocarbons to form the liquid hydrocarbon product.

2. The method of claim 1, wherein disintegrating the hydrocarbon source comprises comminution of the hydrocarbon source.

3. The method of claim 2, wherein comminution comprises grinding.

4. The method of claim 2, wherein comminution comprises high-pressure steam treatment.

5. The method of claim 1, wherein pretreating the disintegrated hydrocarbon source comprises chemical pretreatment, heat pretreatment, oxidation of the hydrocarbon source, or a combination thereof.

6. The method of claim 1, wherein solubilizing the disintegrated hydrocarbon source comprises treating the disintegrated hydrocarbon source with at least one enzyme for breaking cross-linking bonds in the disintegrated hydrocarbon source.

7. The method of claim 1, wherein admixing the biochemical liquor comprises admixing at least one additional enzyme for converting a hydrocarbon source to lower molecular weight hydrocarbons.

8. The method of claim 1, wherein separating the liquid hydrocarbons comprises a process of settling the slurry from the liquid hydrocarbon.

9. The method of claim 1, wherein separating the liquid hydrocarbons comprises settling contaminants from the liquid hydrocarbon.

10. The method of claim 1, wherein enriching the liquid hydrocarbon comprises admixing the liquid hydrocarbon with at least one enzyme for converting lower-valued fractions to higher-valued fractions.

11. The method of claim 1, wherein the biochemical liquor further comprises a modified enzyme.

12. The method of claim 11, wherein the modified enzyme comprises an enzyme that is genetically modified.

13. The method of claim 11, wherein the modified enzyme comprises an enzyme that is chemically modified.

14. The method of claim 1, wherein the method is conducted in-situ in a coal mine or ex-situ on mined coal.

15. The method of claim 1, wherein enriching the liquid hydrocarbons comprises improving the liquid hydrocarbon product qualities prior to distillation.

16. The method of claim 1, wherein the liquid hydrocarbon product comprises at least one selected from the group consisting of gasoline, diesel, kerosene, and distillates thereof.

17. The method of claim 1, wherein the hydrocarbon source comprises at least one selected from the group consisting of coal, anthracite coal, bituminous coal, lignite, sub-bituminous coal, low-rank coals, coke, tar sand, and oil shale.

18. A method for producing a liquid hydrocarbon product comprising,
   disintegrating a hydrocarbon source;
   pretreating the disintegrated hydrocarbon source;
   solubilizing the disintegrated hydrocarbon source to form a slurry comprising a reactant molecule of the hydrocarbon source;
   admixing a biochemical liquor into the slurry, wherein the biochemical liquor comprises at least one conversion enzyme capable of facilitating photo-fragmentation of said reactant molecule of the hydrocarbon source, and wherein the at least one conversion enzyme comprises manganese peroxidase;
   inducing fragmentation of the reactant molecule to form liquid hydrocarbons via enzyme assisted photo-fragmentation with femtosecond laser pulses;
   separating the liquid hydrocarbons from the slurry, wherein contaminants remain in the slurry; and
   enriching the liquid hydrocarbons to form the liquid hydrocarbon product.

* * * * *